United States Patent [19]

Tsou

[11] Patent Number: 5,609,867
[45] Date of Patent: Mar. 11, 1997

[54] POLYMERIC ANTITUMOR AGENTS

[75] Inventor: Hwei-Ru Tsou, Rockland, N.Y.

[73] Assignee: American Cyanamid Company, Madison, N.J.

[21] Appl. No.: 521,505

[22] Filed: Aug. 29, 1995

Related U.S. Application Data

[63] Continuation-in-part of Ser. No. 332,661, Nov. 1, 1994, abandoned.

[51] Int. Cl.[6] ..................... A61K 31/785; A61K 31/765; C08F 9/02
[52] U.S. Cl. ..................... 424/78.36; 424/78.37; 544/232; 544/234; 546/79; 546/81; 514/248; 514/564; 564/459
[58] Field of Search ............................ 424/78.08, 78.36; 544/232, 234; 514/248, 564

[56] References Cited

U.S. PATENT DOCUMENTS

| | | | |
|---|---|---|---|
| 4,520,162 | 5/1985 | Hirano | 525/327.6 |
| 4,526,788 | 7/1985 | Murdock | 524/374 |
| 4,871,528 | 10/1989 | Tognella et al. | 514/922 |
| 5,378,456 | 1/1995 | Tsou | 424/783 |

*Primary Examiner*—Peter F. Kulkosky
*Attorney, Agent, or Firm*—Arnold S. Milowsky

[57] ABSTRACT

This invention provides novel antitumor agents having the formula:

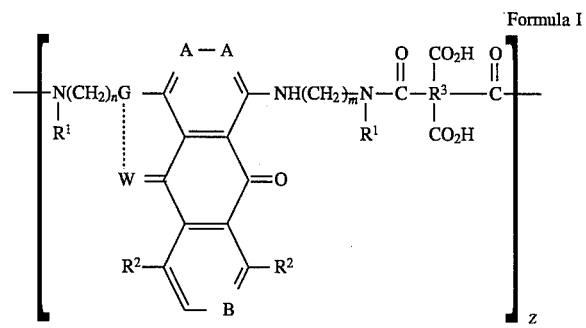

Formula I wherein A, B, G, W, $R^1$, $R^2$, $R^3$, n, m and Z are described in the specification which have activity as anticancer agents and inhibit leukemia and solid tumor growth in a mammal.

13 Claims, 17 Drawing Sheets

Antitumor activity of MITO-BOETDA vs P388 (leukemia) (ip)

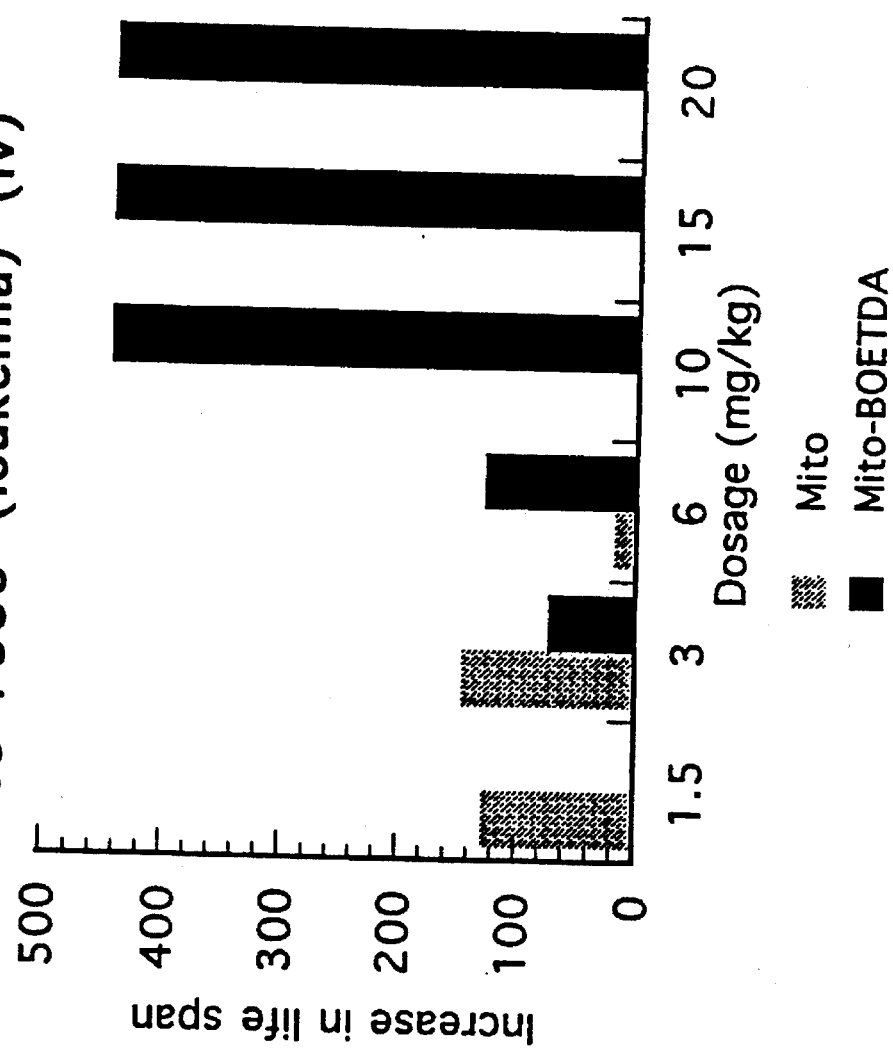

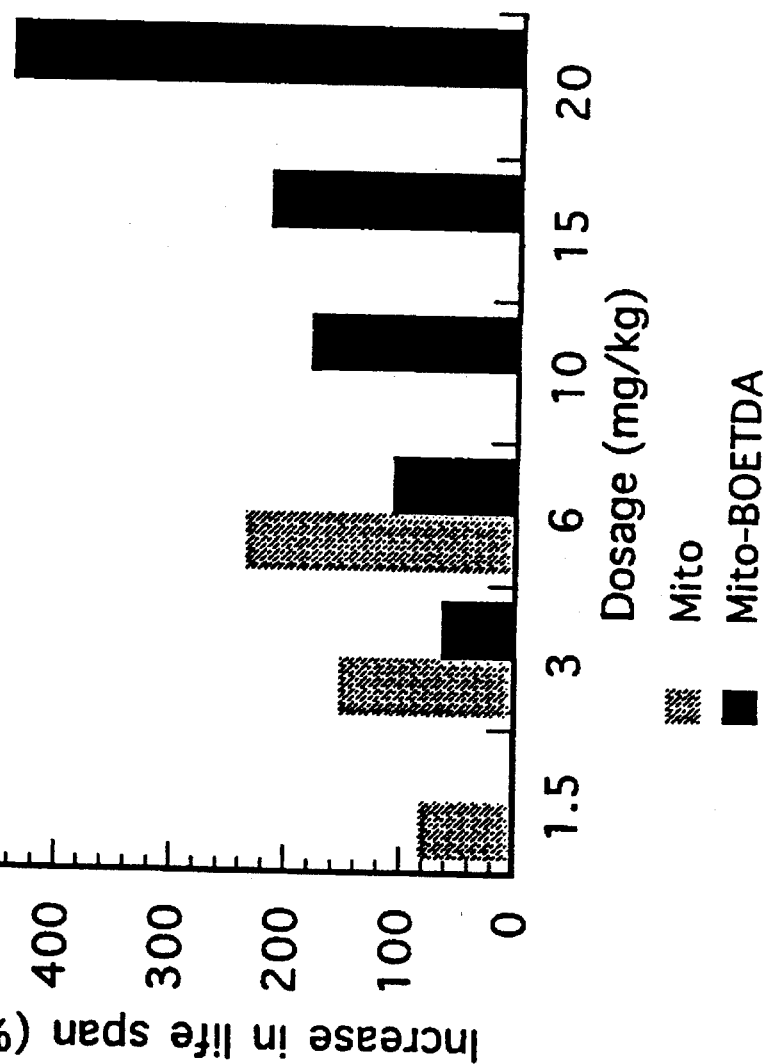

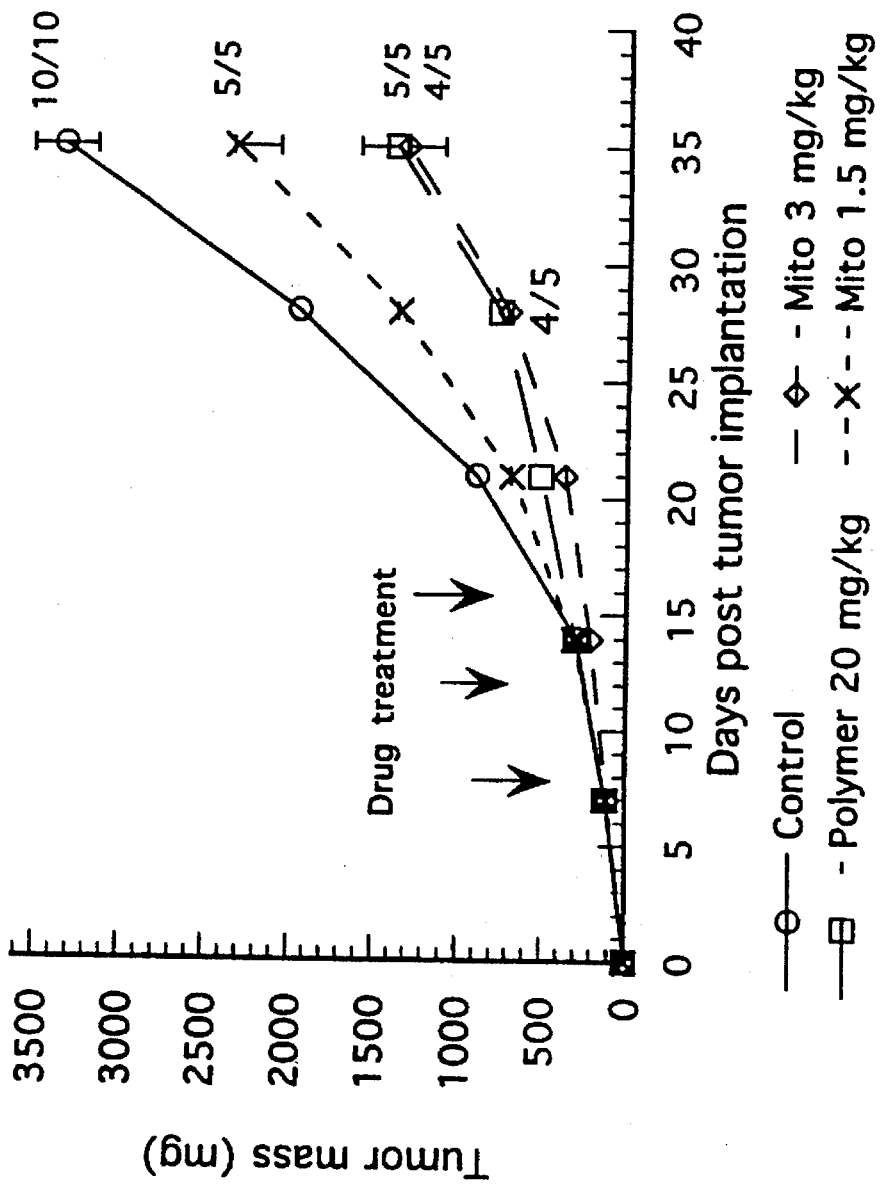

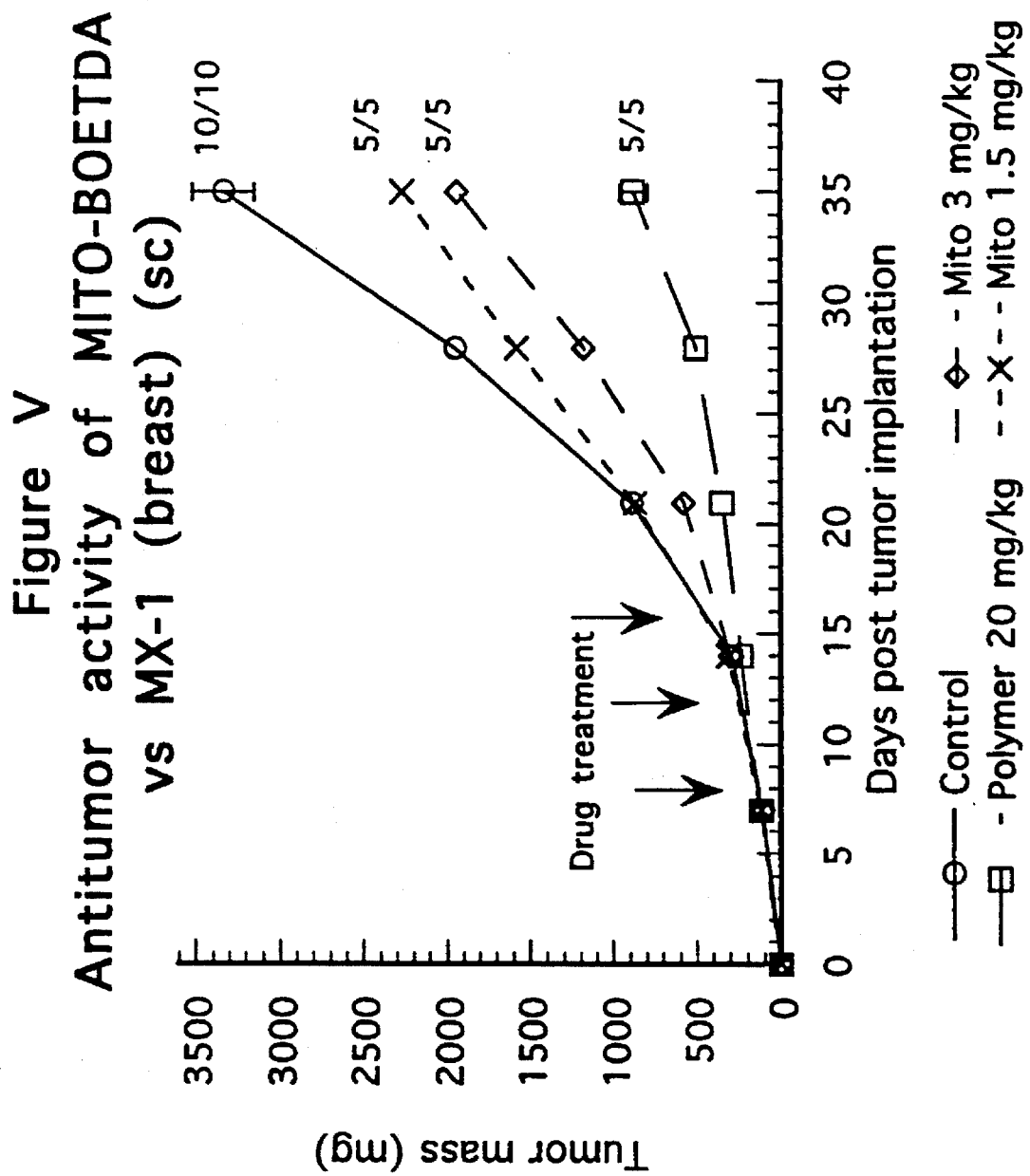

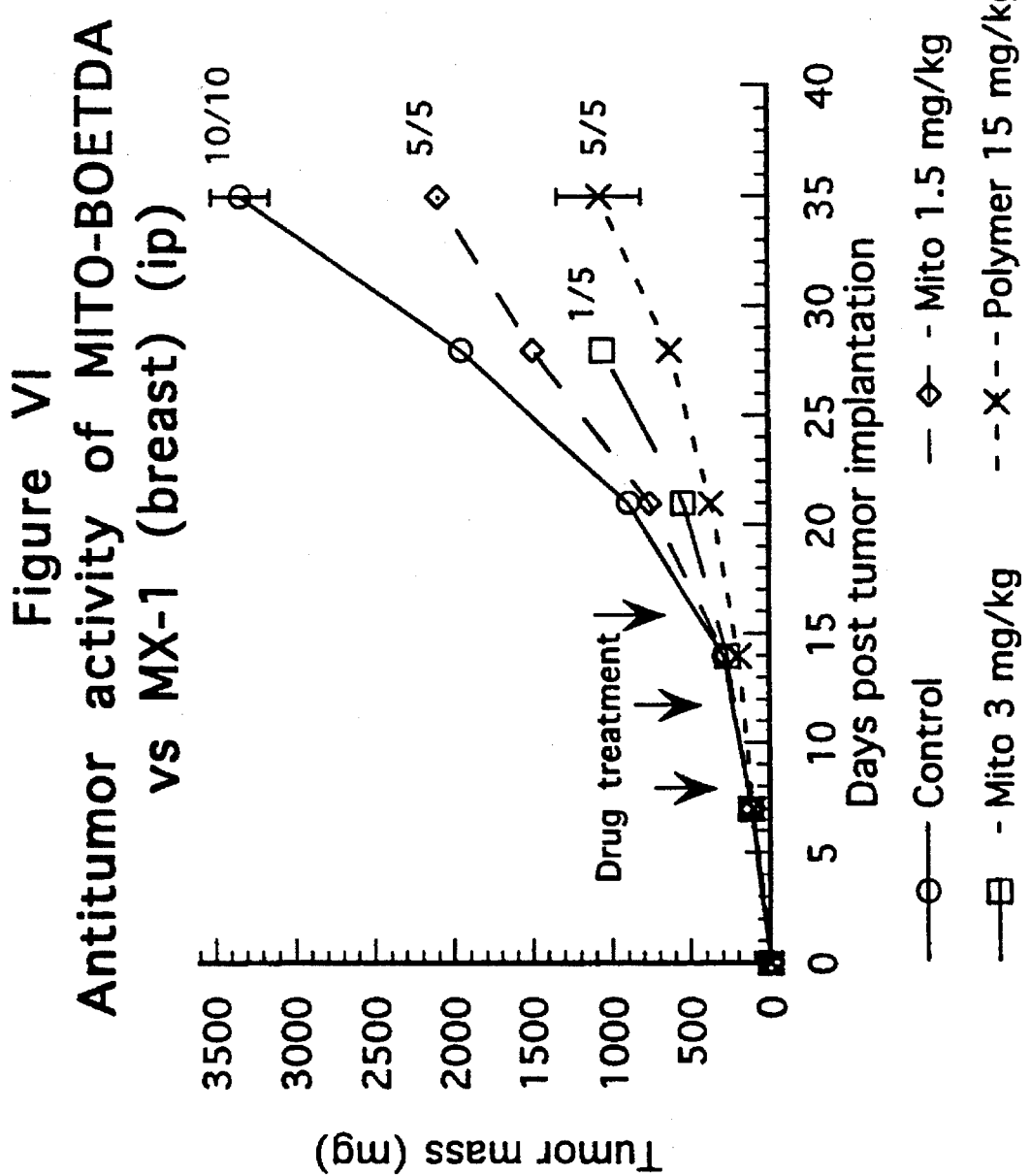

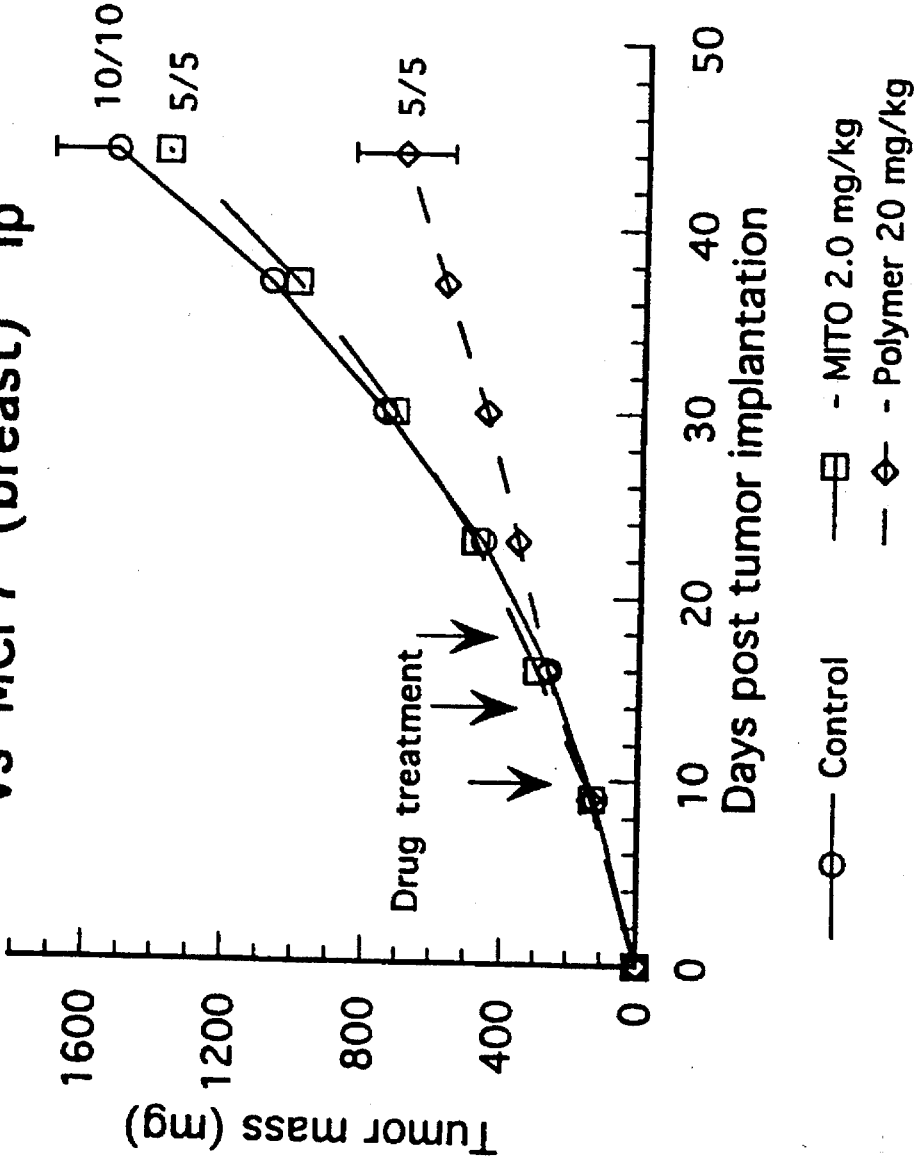

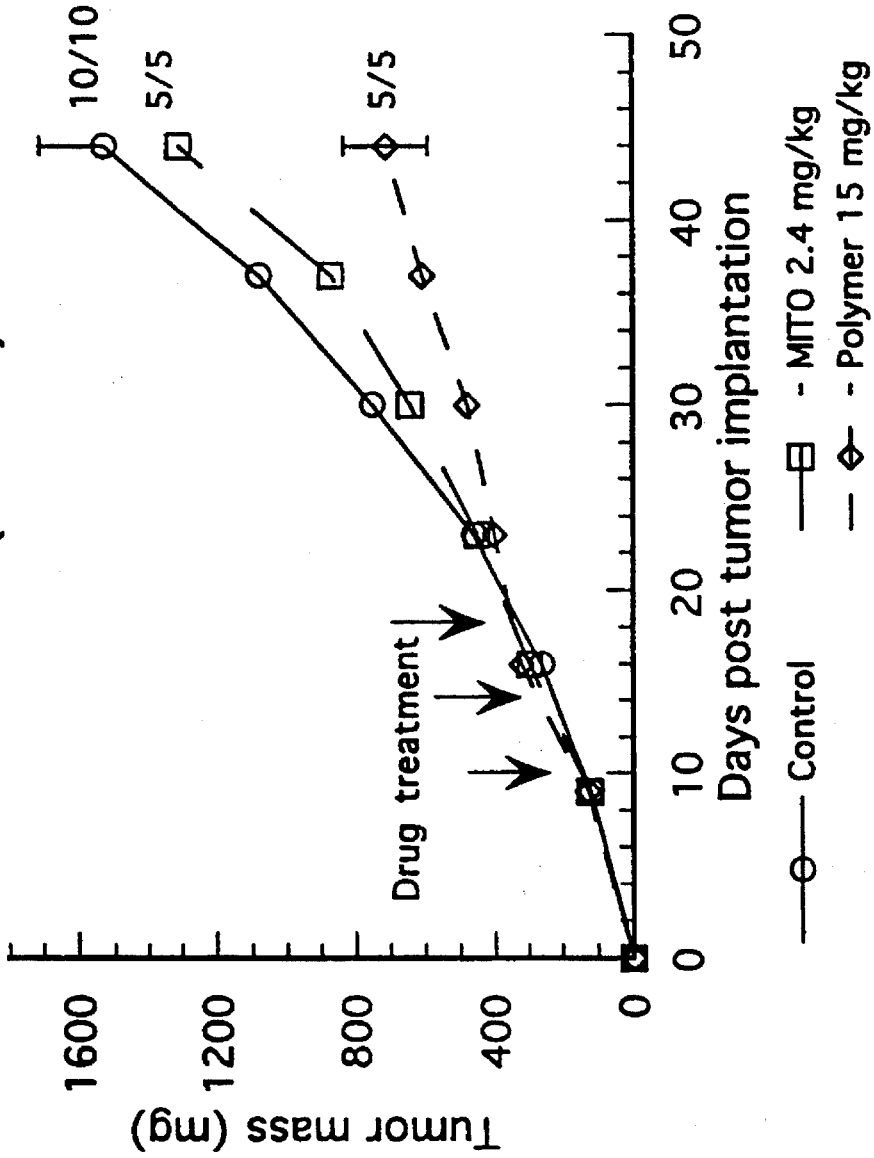

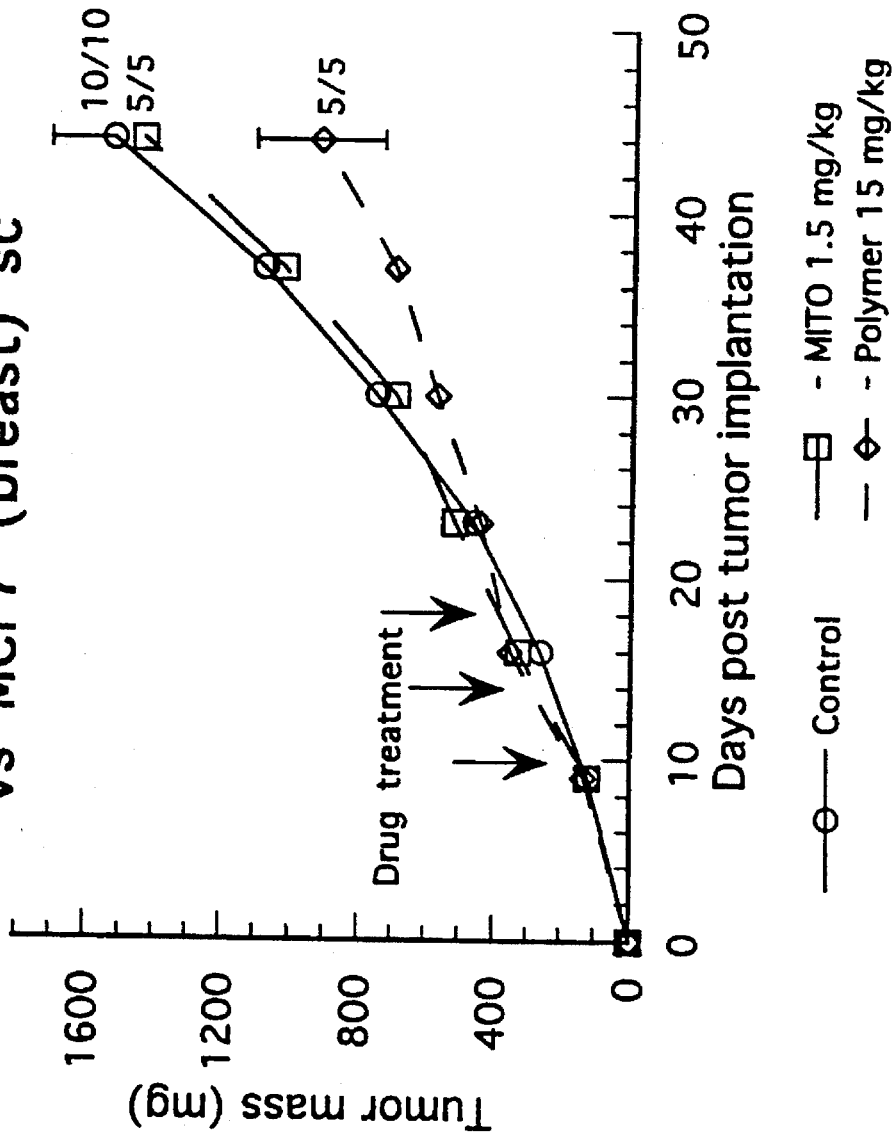
Figure IX
Antitumor activity of MITO-BOETDA vs MCF7 (breast) sc

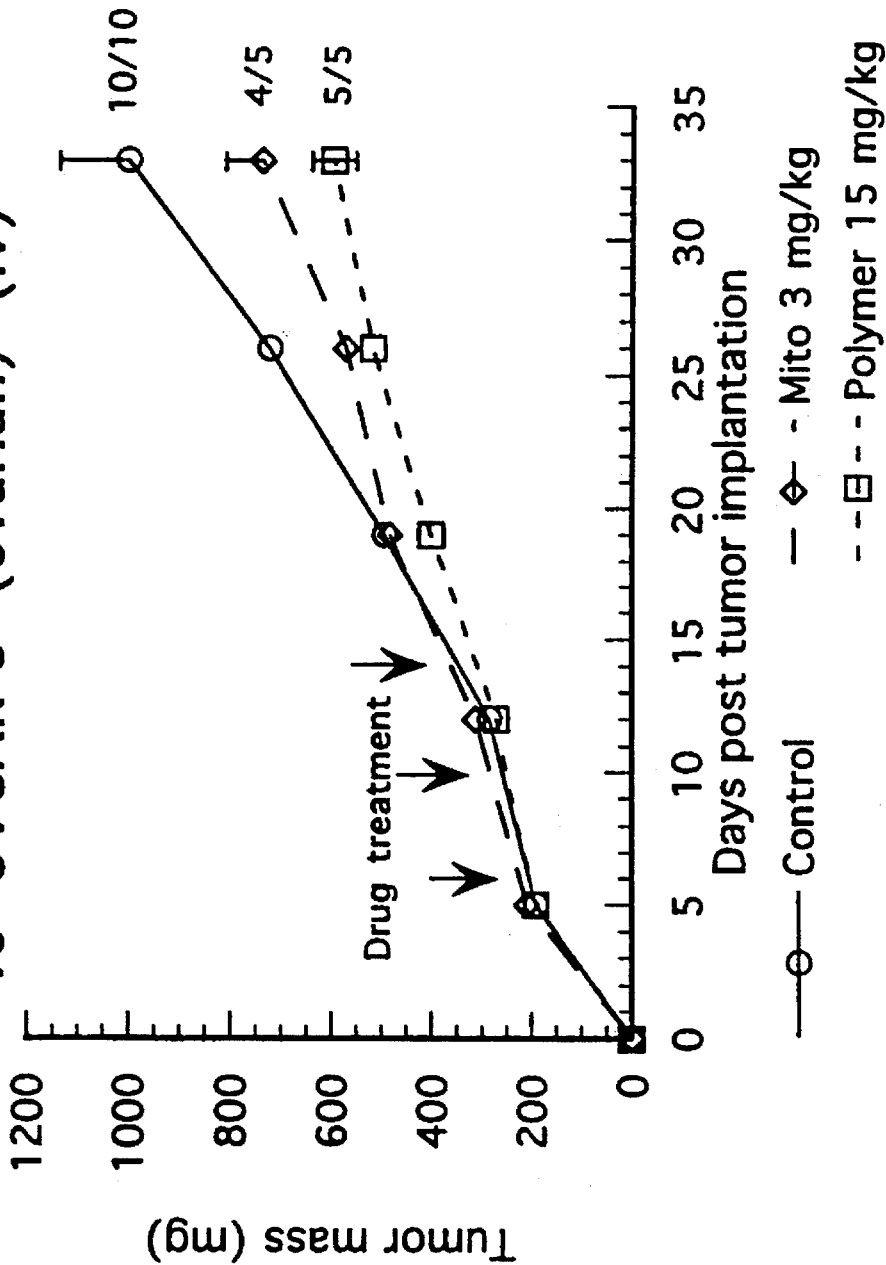

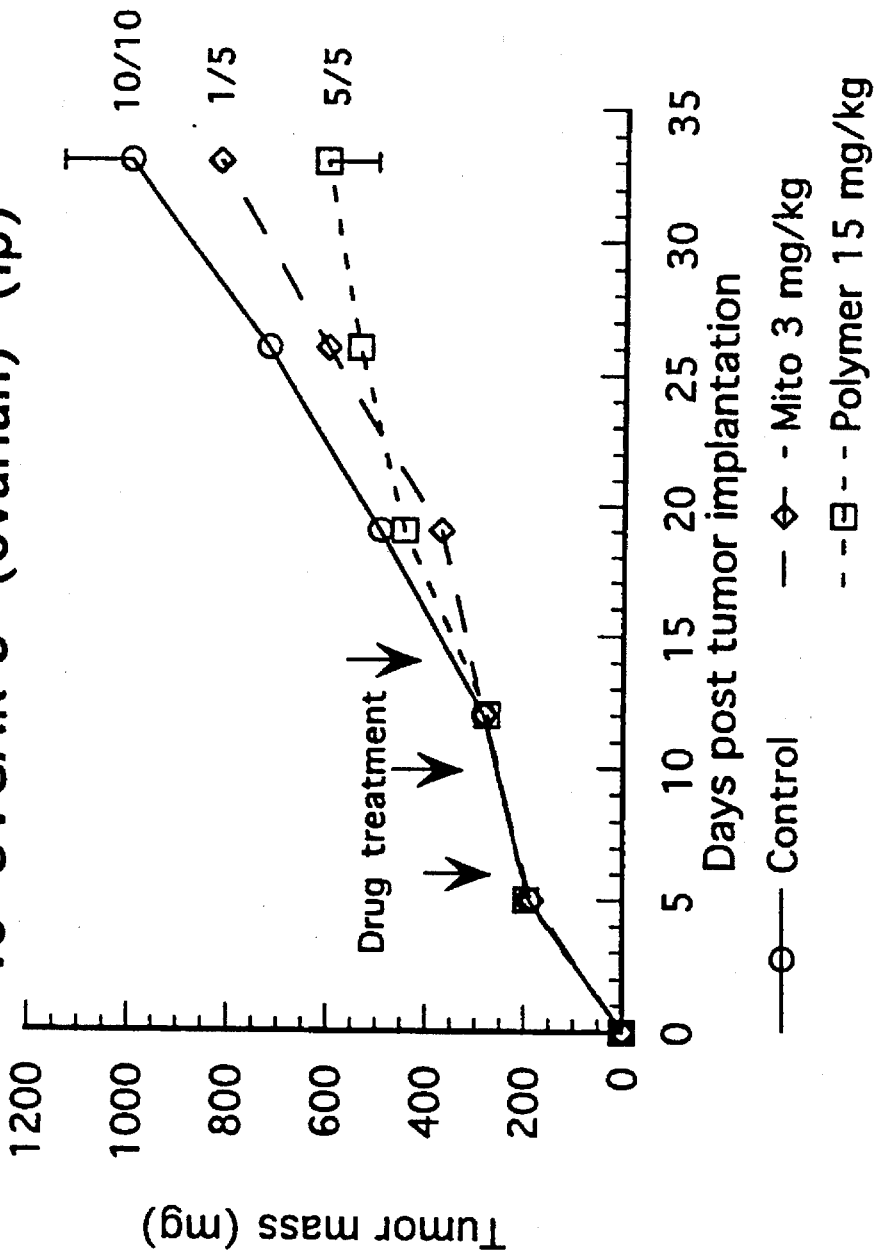

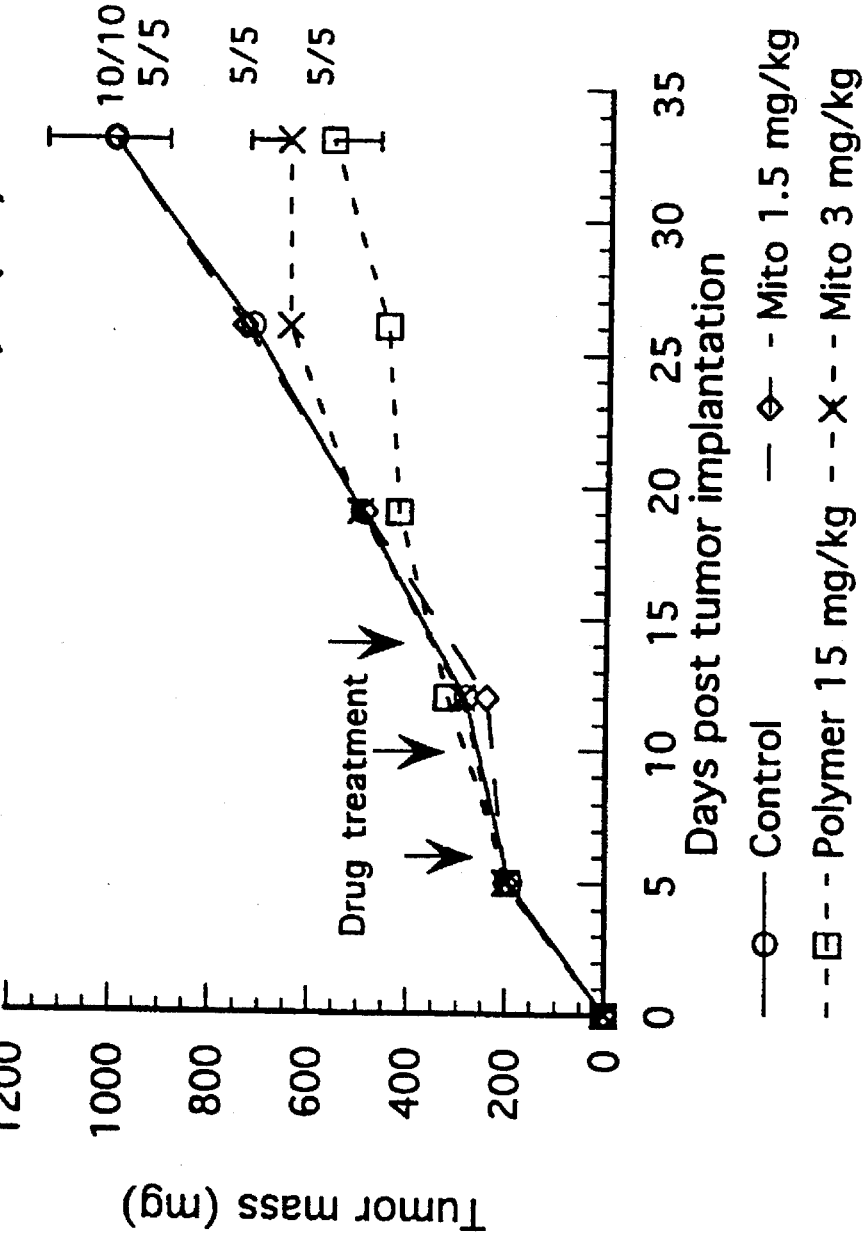
Figure XII
Antitumor activity of MITO-BOETDA vs OVCAR-3 (ovarian) (sc)

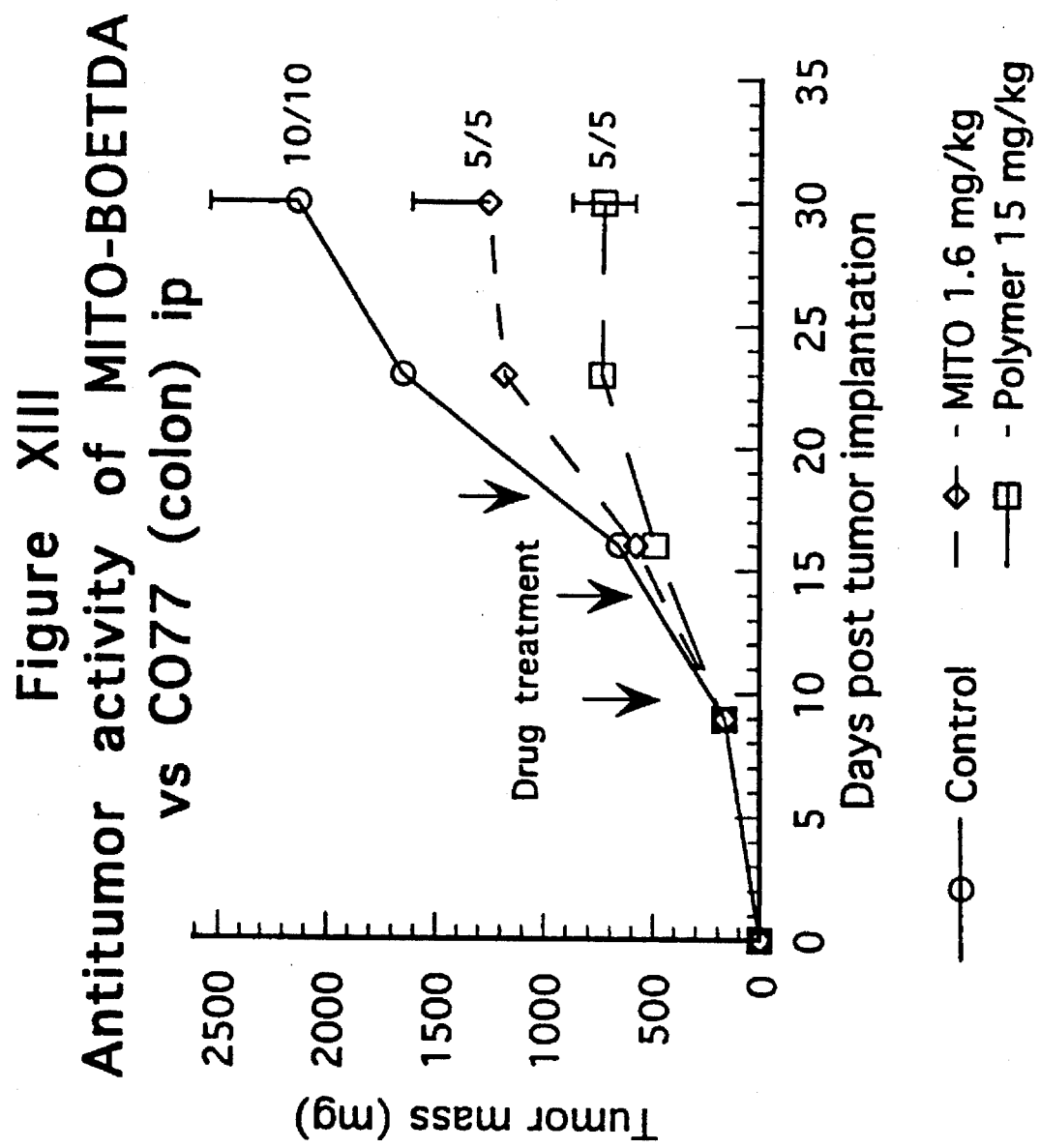

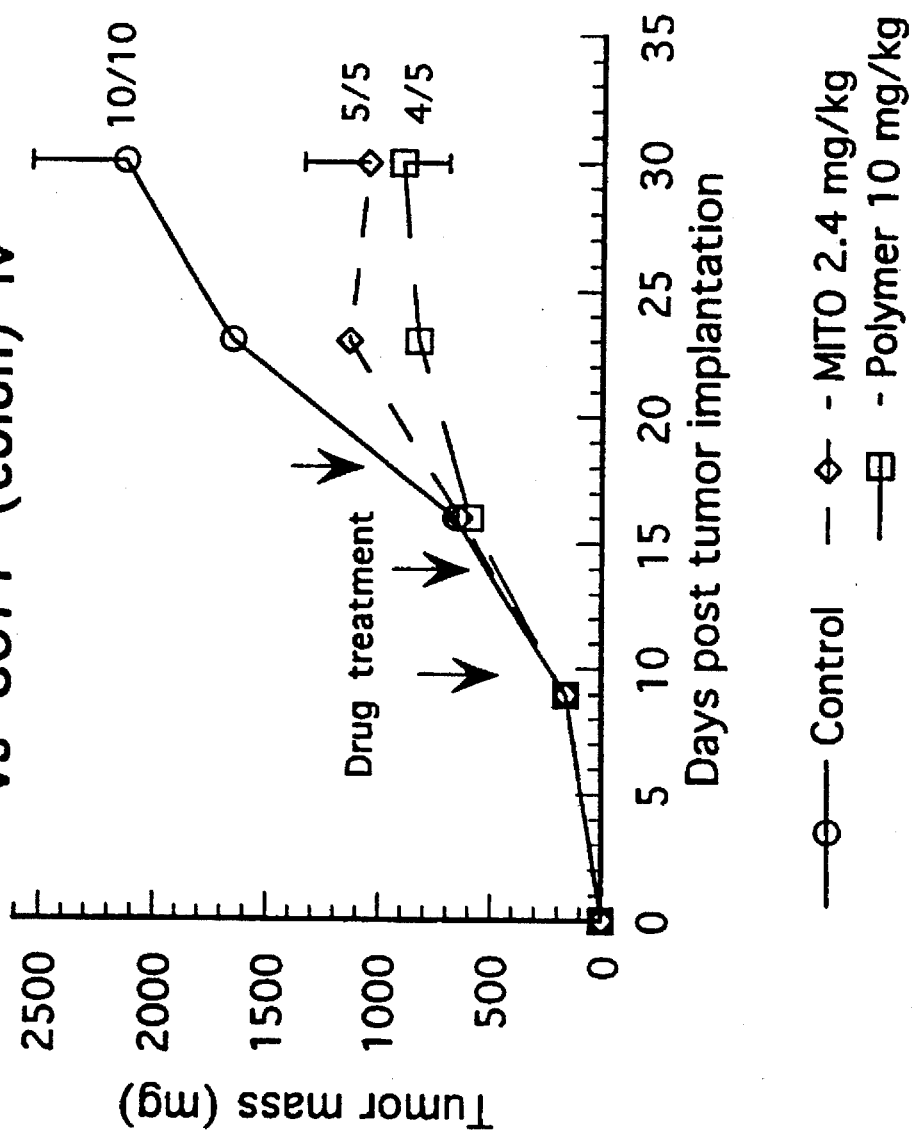

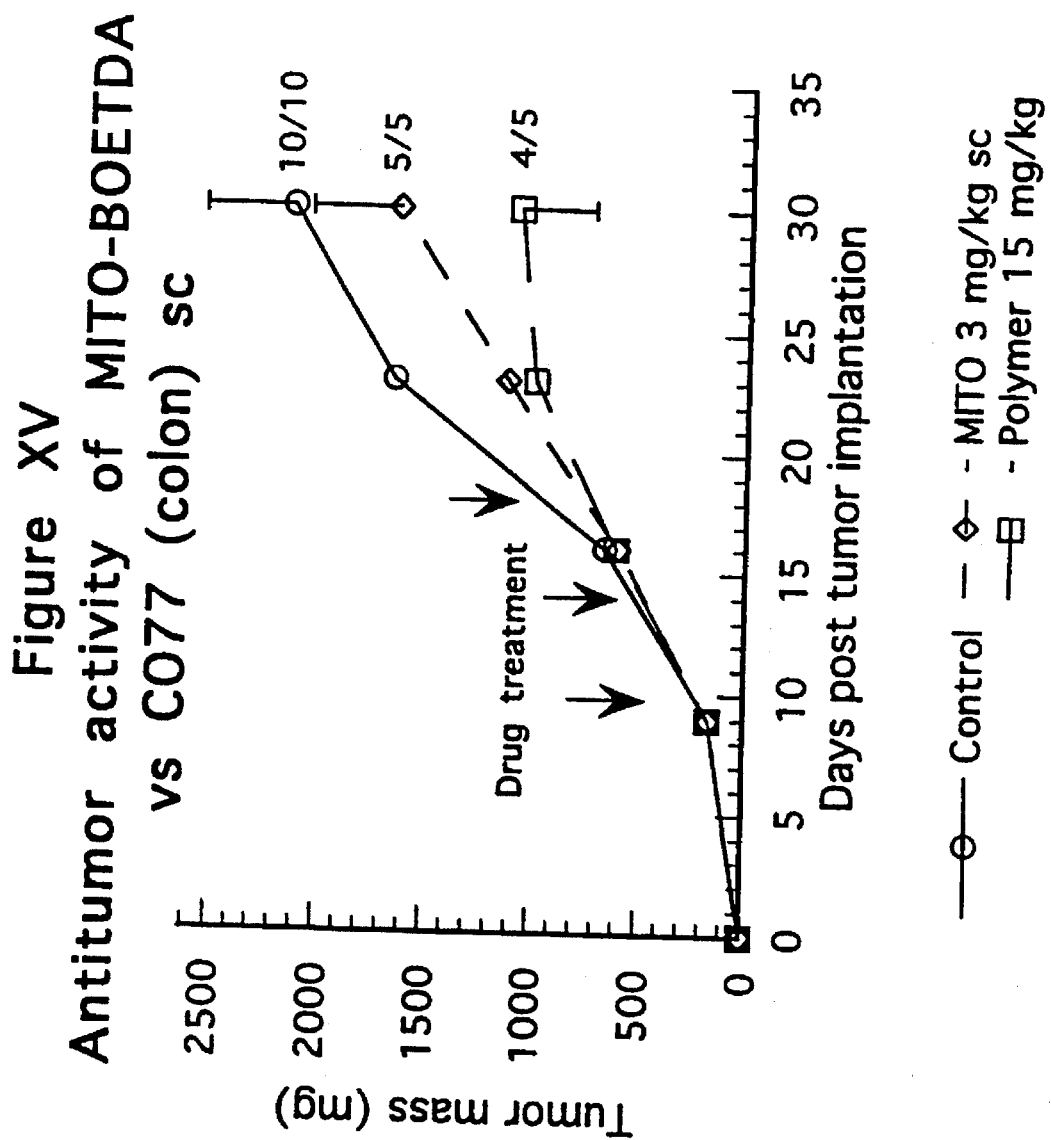

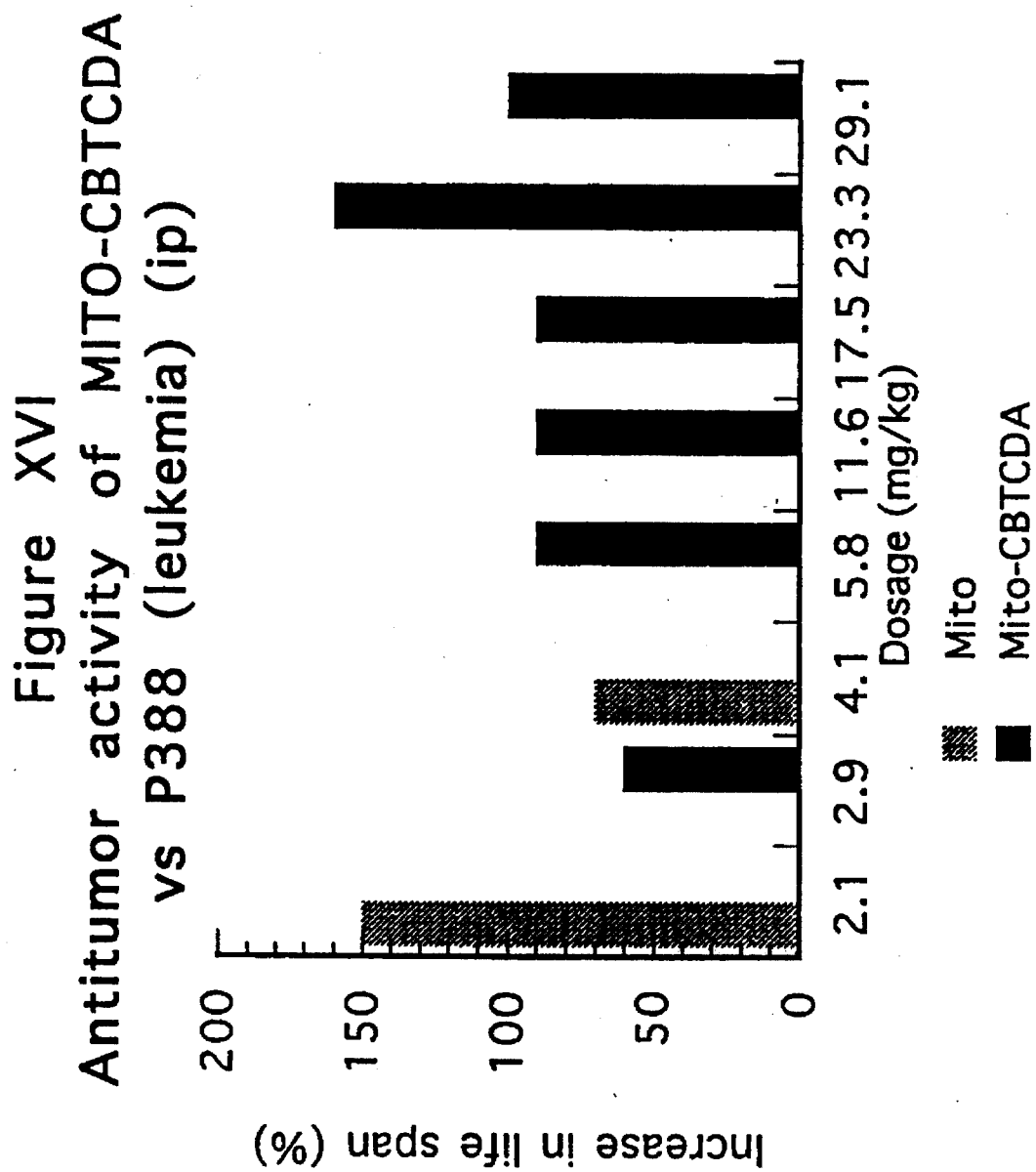

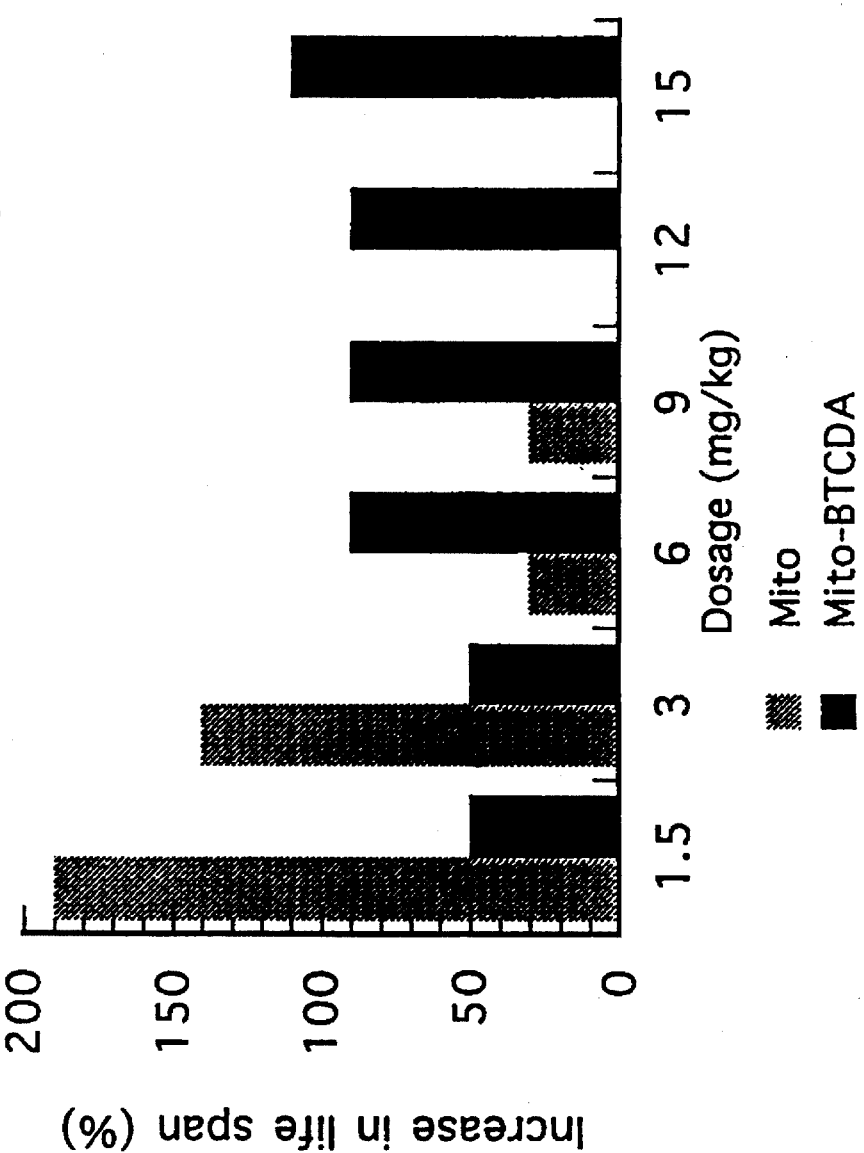

POLYMERIC ANTITUMOR AGENTS

This is a continuation-in-part of U.S. Ser. No. 08/332,661, filed Nov. 1, 1994, now abandoned.

BACKGROUND OF THE INVENTION

1. Field of the Invention

This invention relates to new organic compounds and, more particularly, is concerned with novel polymeric 1,4-bis-[(cyclic-substituted)alkylamino]anthraquinone, anthrapyrazole, aza-anthraquinone and diaza-anthraquinone compounds which are active as anticancer agents and inhibit tumor growth in a mammal.

More particularly, the invention relates to the preparation and use of copolymers which are synthesized from anthraquinone, anthrapyrazole, aza-anthraquinone and diaza-anthraquinone monomers copolymerized with another monomer, namely, a dianhydride molecule.

2. Description of the Related Art

Macromolecules have been used as drug carriers in an attempt to prolong plasma levels of drugs presumably through slow release of drugs from macromolecules, and to achieve favorable uptake by the tumor cells. Among macromolecular carriers, divinyl ethermaleic anhydride (MVE) copolymer has been investigated extensively. MVE copolymer contains multiple anhydride rings, which allow easy functionalization with antitumor agents carrying nucleophilic groups such as $-NH_2$, $-OH$, and $-SH$. Furthermore, a carboxyl group is generated when each anhydride ring is functionalized with a drug molecule. Therefore, MVE copolymer is capable of covalently binding a large number of lipophilic antitumor agents, while maintaining water solubility.

MVE copolymer has been linked covalently with various therapeutically active antitumor agents including 5-fluorouridine, daunomycin, adriamycin, β-D-arabinofuranosylcytosine and methotrexate with varying results. Some of the MVE-linked agents demonstrated higher therapeutic efficacies and lower toxicities during in vivo antitumor evaluations while others showed no increase in efficacy relative to the parent drugs.

U.S. Pat. No. 4,520,162 discloses that MVE copolymer linked with adriamycin showed significantly higher therapeutic efficacies and lower toxicities than adriamycin, whereas daunomycin conjugated with MVE copolymer gave only marginal benefit than daunomycin. Also, attachment of MVE copolymer to a different site on the same antitumor drug yields conjugates with different antitumor activity. For example, adriamycin conjugated to MVE copolymer via amide linkages (U.S. Pat. No. 4,520,162) shows higher antitumor activity than the corresponding conjugate via ester linkages (Belgian Patent 902,344). Furthermore, U.S. Pat. No. 4,520,162 demonstrated that different degree of drug conjugation (i.e., arabinofuranosylcytosine) also gives different effect on the antitumor activity.

The anthraquinones, anthrapyrazoles, aza-anthraquinones and diaza-anthraquinones useful in this invention are a group of compounds having an anthracene moiety of which mitoxantrone is a representative member. Mitoxantrone is indicated for treatment of acute nonlymphocytic leukemia, and breast tumors (in Canada and other countries, but not the U.S.) in humans. While these agents exhibit excellent antitumor activity, they also exhibit toxicity to normal cells. For example, administration of mitoxantrone is associated with myelosuppression as well as other side effects.

In one copending application, Ser. No. 037,149, filed Mar. 25, 1993, synthetic anthracene antineoplastic compounds are covalently conjugated with, or in admixture with, a hydrolyzate of a co-polymeric moiety of divinyl ether and maleic anhydride (MVE) and show higher antitumor activity than either agent exhibits when administered alone.

U.S. Pat. No. 4,526,788 describes novel polymeric 1,4-bis-[(1,3-oxazolidin-3-yl)alkylamino]anthraquinones prepared by condensation of 1,4-bis-[(2-hydroxyalkylamino)alkylamino]anthraquinones with dialdehydes which are useful as anticancer agents. However, this series of polymers is not water-soluble. The polymer has to be administered to mammals intraperitoneally as a suspension. Furthermore, this series of polymers is only tested against lymphocytic leukemia P388 and melanotic melanoma B16 in mammals.

The present invention provides a method to prepare water-soluble polymers allowing easy administration by intravenous route in addition to intraperitoneous route. These novel polymers potentiate the antitumor activity of anthraquinones, anthrapyrazoles, aza-anthraquinones and diaza-anthraquinones. In comparison with the parent drug, the polymers have higher antitumor activities and better therapeutic index against not only P388 leukemia, but also some solid tumors in mammals.

SUMMARY OF THE INVENTION

According to the present invention, there are provided novel compounds of Formula I which have antitumor activities and are useful for treating cancer

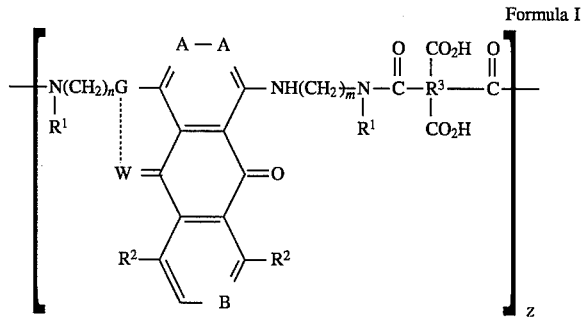

Formula I wherein:
A and B are CH or N and when B is N, A is CH;
W is O or N and when W is O, G is NH and when W is N, G is N and the dotted line is a bond;
$R^1$ is the same or different and selected from H, $-(CH_2)_n-$OH, straight or branched lower alkyl($C_1-C_4$) and carbocyclic rings of 3, 4, 5, 6, or 7 carbon atoms;
$R^2$ is the same or different and selected from H, OR, halogen, or $-NRR'$;
R and R' are the same or different and selected from H, lower alkyl($C_1-C_4$);
m and n are the same or different and are 2 or 3;
Z is 1 to 100;
the moiety

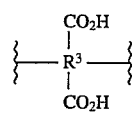

is:

(1) a phenyl having the structure:

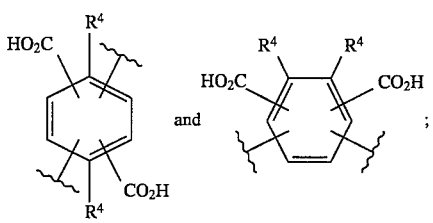

wherein each carboxylic acid group is adjacent to the ring carbon bearing the substituent attached to the polymer backbone;

$R^4$ is the same or different and selected from H, $CF_3$, and phenyl;

(2) a naphthalene having the structure:

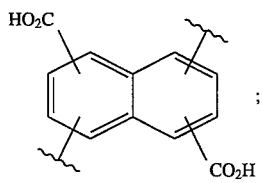

wherein each carboxylic acid group is adjacent to the ring carbon bearing the substituent attached to the polymer backbone;

(3) a cyclobutane having the structure:

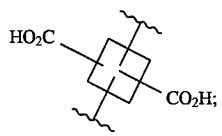

(4) a bicyclic ring having the structures:

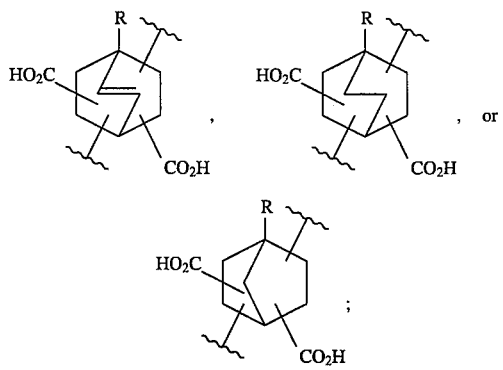

where R is as hereinbefore defined;

(5) a ring system having the structures:

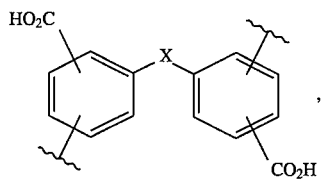

-continued

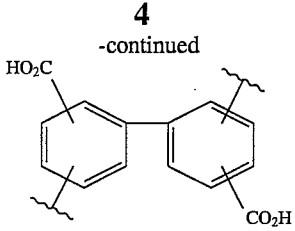

X=O, CO, $C(CF_3)_2$, $CH_2$, $SO_2$, or 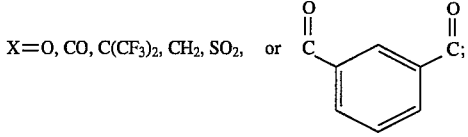

wherein each carboxylic acid group is adjacent to the ring carbon bearing the substituent attached to the polymer backbone.

(6) a hydroquinone having the structure:

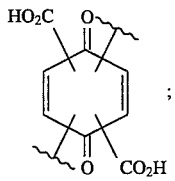

and pharmaceutically acceptable salts of these compounds.

The present invention also provides methods of making and using the novel polymeric 1,4-bis-[(cyclic-substituted) alkylamino]anthraquinone, anthrapyrazole aza-anthraquinone and diaza-anthraquinone compounds for treating cancer. The anthraquinone, anthrapyrazole aza-anthraquinone and diaza-anthraquinone compounds are selected from antineoplastic compounds such as 5,8-dihydroxy-1,4-bis[[2-[(2-hydroxyethyl)amino)ethyl]amino]-9, 10-anthracenedione dihydrochloride (mitoxantrone), 1,4-bis [(2-aminoethyl)amino]-5,8-dihydroxyanthraquinone dihydrochloride, 9,10-anthracenedicarboxaldehyde bis(2-imidazolin-2-ylhydrazone) (bisantrene), 2,5-bis[[2-[(2-hydroxyethyl)-amino]ethyl]amino]-7-hydroxy-anthra[1,9-cd] pyrazole -6(2H)-one, 6,9-bis[(2-aminoethyl -amino]-benzo [g]isoquinoline-5,10-dione and 1,4-bis[N-(2-(2-hydroxyethylamino)ethyl) amino]-2,3-diaza-anthracene-9, 10-dione and homologs, isomers and analogs thereof.

The covalently conjugated compounds show higher antitumor activities than the monomers alone. The polymers show antitumor activities against some tumors to which the monomers alone are inactive. A polymer of the invention poly[[(2-hydroxyethyl)-imino]carbonyl(3,6-dicarboxybicyclo[2.2.2]octa-7-ene -2,5-diyl)carbonyl[(2-hydroxyethyl)imino]-1,2-ethanediylimino (9,10-dihydro-5,8-dihydroxy-9,10-dioxo-1,4-anthracenediyl)imino-1,2-ethanediyl disodium salt] is referred to herein as MITO-BOETDA. A polymer of the invention poly[[(2

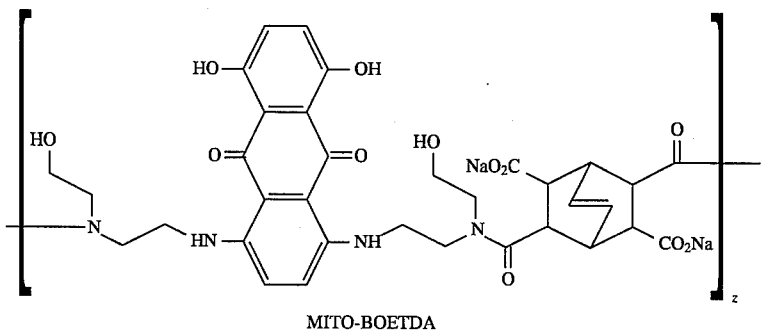

MITO-BOETDA

-hydroxyethyl)imino]carbonyl-2,4-dicarboxy-1,3-cyclobutanediyl) carbonyl[(2-hydroxyethyl)imino]-1,2-ethanediylimino (9,10-dihydro-5,8-dihydroxy-9,10-dioxo-1,4-anthracenediyl)imino-1,2-ethanediyl disodium salt] is referred to herein as MITO-CBTCDA. A polymer of the invention

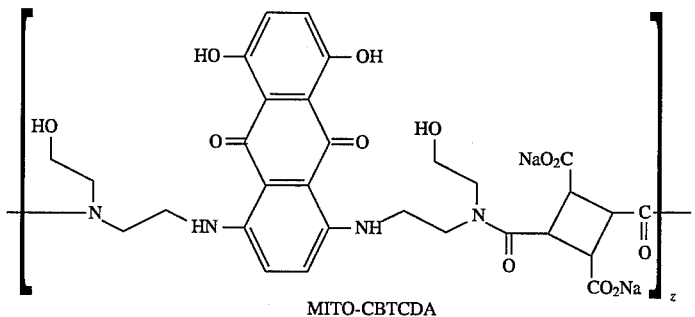

MITO-CBTCDA poly [[(2-hydroxyethyl)imino]carbonyl-2,5-dicarboxy-1,4-phenylene)carbonyl [(2-hydroxyethyl)imino]-1,2-ethanediylimino(9,10-dihydro-5,8-dihydroxy-9,10-dioxo-1,4-anthracenediyl)imino-1,2-ethanediyl disodium salt] is referred to herein as MITO-BTCDA.

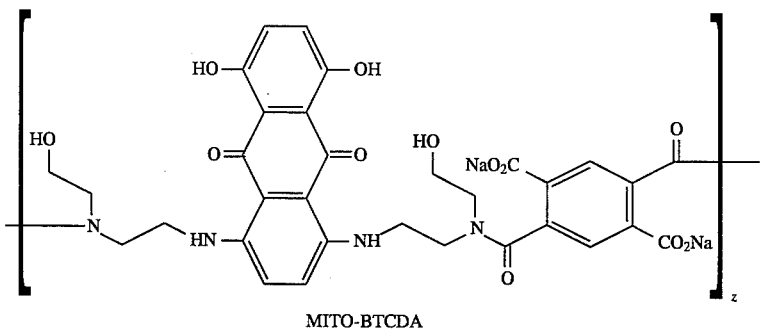

MITO-BTCDA

BRIEF DESCRIPTION OF THE DRAWINGS

FIG. I is a graph illustrating the percent increase in life span (% ILS) of mice treated with mitoxantrone as compared to MITO-BOETDA copolymer in the P388 tumor model by intraperitoneal (ip) administration. as compared to MITO-BOETDA copolymer in the P388 tumor model by intraperitoneal(ip) administration.

FIG. II is a graph illustrating the percent increase in life span (% ILS) of mice treated with mitoxantrone as compared to MITO-BOETDA copolymer in the P388 tumor model by intravenous(iv) administration.

Figure 1:
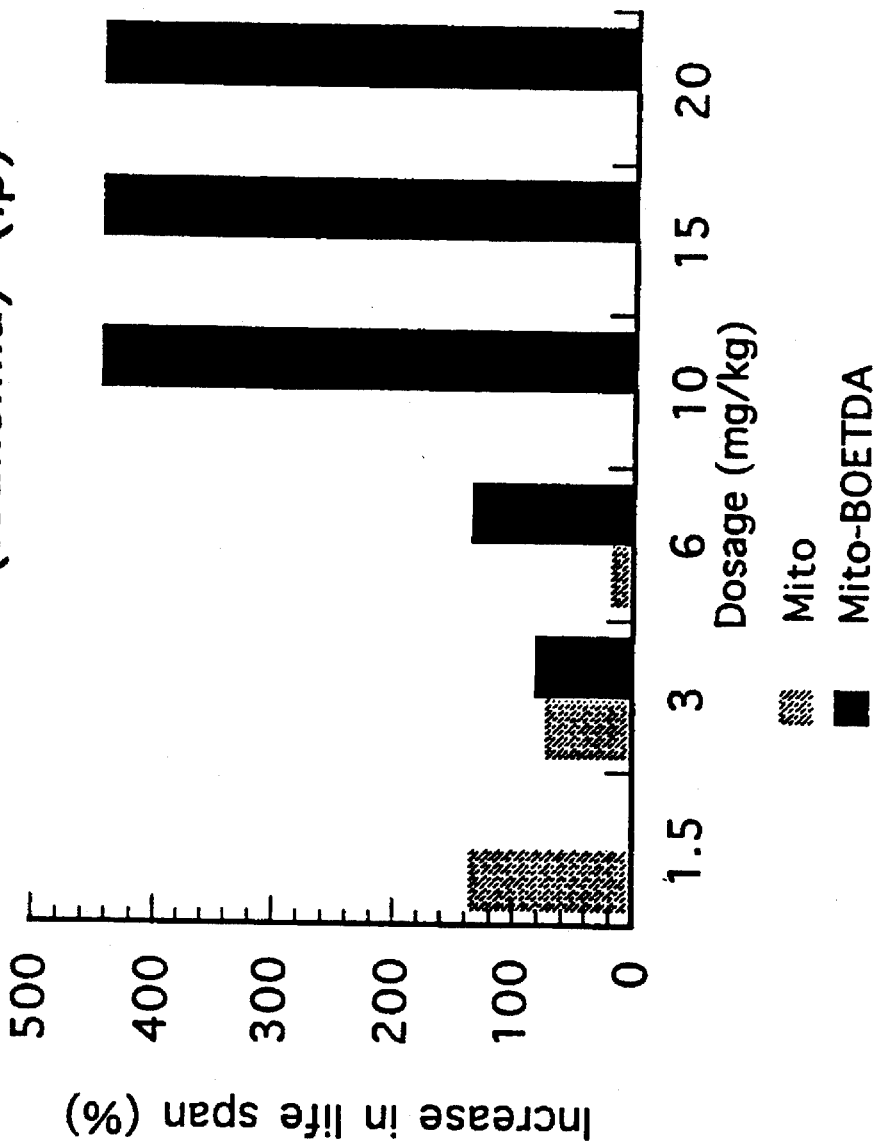

FIG. III is a graph illustrating the percent increase in life span (% ILS) of mice treated with mitoxantrone as compared to MITO-BOETDA copolymer in the P388 tumor model by subcutaneous(sc) administration.

FIG. IV is a graph illustrating the decrease in-MX-1 tumor mass in mice when treated with mitoxantrone vs. MITO-BOETDA copolymer vs. control by intravenous (iv) administration.

FIG. V is a graph illustrating the decrease in MX-1 tumor mass in mice when treated with mitoxantrone vs. MITO-BOETDA copolymer vs. control by subcutaneous(sc) administration.

FIG. VI is a graph illustrating the decrease in FIX-1 tumor mass in mice when treated with mitoxantrone vs. MITO-BOETDA copolymer vs. control by intraperitoneal(ip) administration.

FIG. VII is a graph illustrating the decrease in MCF7 tumor mass in mice when treated with mitoxantrone vs. MITO-BOETDA control vs. control by intraperitoneal (ip) administration.

FIG VIII is a graph illustrating the decrease in MCF7 tumor mass in mice when treated with mitoxantrone vs. MITO-BOETDA copolymer vs. control by intravenous (iv) administration.

FIG. IX is a graph illustrating the decrease in MCF7 tumor mass in mice when treated with mitoxantrone vs. MITO-BOETDA copolymer vs. control by subcutaneous(sc) administration.

FIG. X is a graph illustrating the decrease in OVCAR-3 tumor mass in mice when treated with mitoxantrone vs. MITO-BOETDA copolymer vs. control by intravenous (iv) administration.

FIG. XI is a graph illustrating the decrease in OVCAR-3 tumor mass in mice when treated with mitoxantrone vs. MITO-BOETDA copolymer vs. control by intraperitoneal (ip) administration.

FIG. XII is a graph illustrating the decrease in OVCAR-3 tumor mass in mice when treated with mitoxantrone vs. MITO-BOETDA copolymer vs. control by subcutaneous (sc) administration.

FIG. XIII is a graph illustrating the decrease in colon 77 tumor mass in mice when treated with mitoxantrone vs. MITO-BOETDA copolymer vs. control by intraperitoneal (ip) administration.

FIG. XIV is a graph illustrating the decrease in colon 77 tumor mass in mice when treated with mitoxantrone vs. MITO-BOETDA copolymer vs. control by intravenous (iv) administration.

FIG. XV is a graph illustrating the decrease in colon 77 tumor mass in mice when treated with mitoxantrone vs. MITO-BOETDA copolymer vs. control by subcutaneous (sc) administration.

FIG. XVI is a graph illustrating the percent increase in life span (% ILS) of mice treated with mitoxantrone as compared to MITO-CBTCDA copolymer in the P388 tumor model by intraperitoneal (ip) administration.

FIG. XVII is a graph illustrating the percent increase in life span (% ILS) of mice treated with mitoxantrone as compared to MITO-BTCDA copolymer in the P388 tumor model by intraperitoneal (ip) administration.

DETAILED DESCRIPTION OF THE INVENTION

The novel compounds of the present invention are prepared according to the following reaction Scheme I.

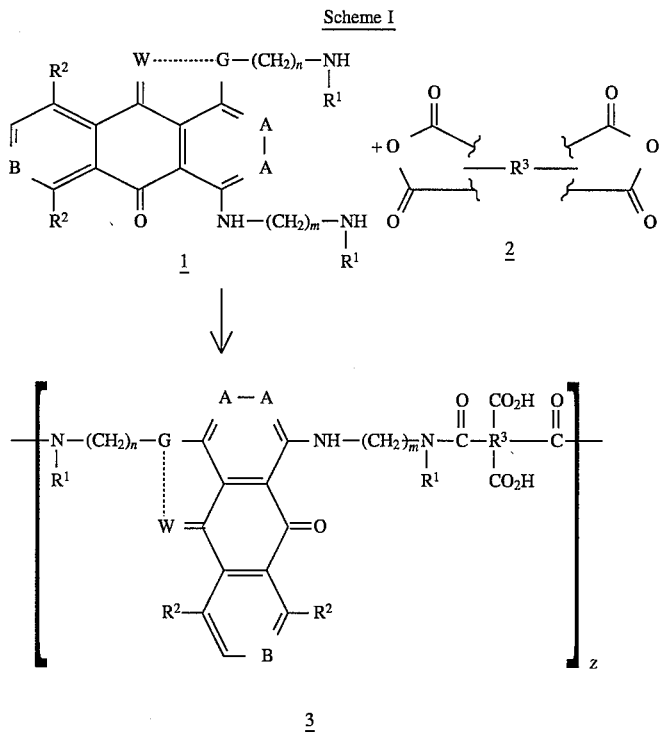

Referring to Scheme I, the corresponding 1,4-disubstituted-anthraquinone, anthrapyrazole, aza-anthraquinone or diaza-anthraquinone 1, wherein A, B, G, W, $R^1$, $R^2$, n, m and Z are hereinbefore defined, is reacted with symmetrical dianhydride 2, wherein $R^3$ represents:

(1) a phenyl ring having the structures:

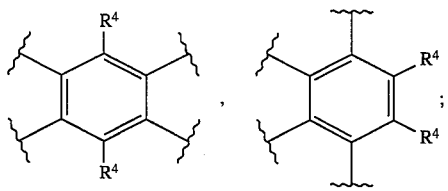

wherein $R^4$ is the same or different and selected from H, $CF_3$ or phenyl;

(2) a naphthalene having the structures:

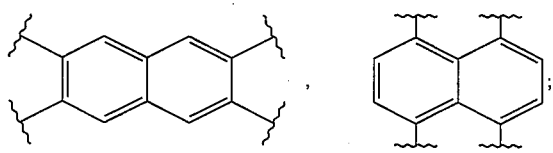

(3) a cyclobutane ring having the structure:

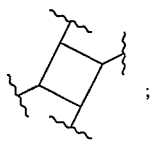

(4) a bicyclic ring having the structures, where R is hereinbefore defined:

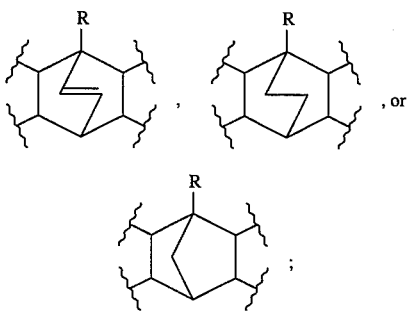

(5) a ring system having the structures:

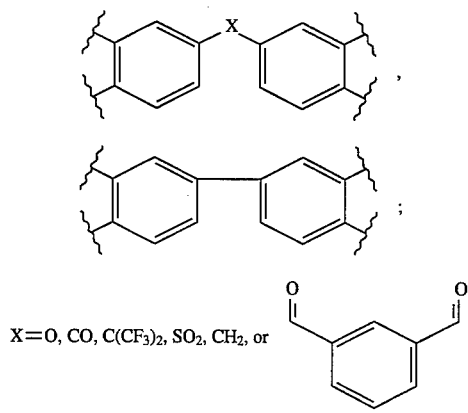

X=O, CO, C(CF$_3$)$_2$, SO$_2$, CH$_2$, or (6) a hydroquinone having the structure:

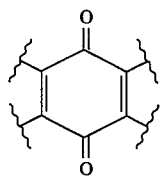

in 1-methyl-2-pyrrolidinone, dimethylformamide, N,N-dimethylacetamide, dimethylsulfoxide and the like, at temperature of 10°–60° C. for 10 to 48 hours to give copolymer 3. The adjustment of the pH to 7.0–7.5 by the addition of aqueous sodium bicarbonate to 3 gives the sodium salt. Lyophilization of the aqueous solution gives the sodium salt of 3 as a powder.

As stated above, the covalent conjugates of the invention may be prepared by reacting the appropriate dianhydride with the anthraquinone, anthrapyrazole, aza-anthraquinone and diaza-anthraquinone antitumor agent in a suitable organic solvent such as 1-methyl-2-pyrrolidinone, dimethylsulfoxide, dimethylformamide, N,N-dimethylacetamide and the like, to form the amide linkage between the amino group of the anthraquinone, anthrapyrazole, aza-anthraquinone and diaza-anthraquinone agents and the carbonyl group of the anhydride moiety. Following complete hydrolysis to form the free acid form, it may be converted to the salt form with a variety of pharmacologically acceptable salt forming reagents containing a salt forming cation such as sodium, potassium, calcium, magnesium, ammonium and the like.

Pharmaceutically suitable salts include both the metallic (inorganic) salts and organic salts; a list of which is given in *Remington's Pharmaceutical Sciences*, 17th Edition, pg. 1418(1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

Relative to the above generic description, compounds of Formula I which are preferred are those in which $R^1$ is —(CH$_2$)$_n$OH, H, or lower alkyl(C$_1$–C$_4$);

$R^2$ is hydroxy;

the moiety

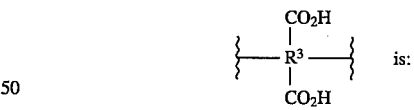

is:

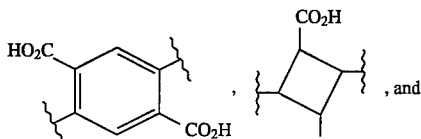

, and

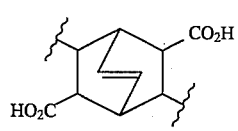

n is 2; and

Z is 1 to 100.

Examples of compounds for use as starting materials in the present invention are those having the anthracene nucleus of which mitoxantrone is a well known example. Mitoxantrone has the following structural formula:

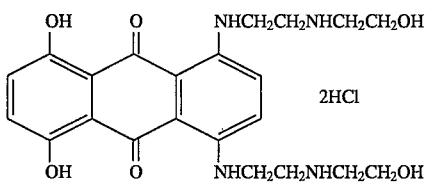

Mitoxantrone may be prepared in accordance with the disclosure of U.S. Pat. No. 4,197,249, hereby incorporated by reference into the present application. This compound is known as an excellent antitumor agent in the treatment of acute nonlymphocytic leukemia. The compound is now in clinical trials for treating ovarian cancer. The preferred compounds for use in the present invention are mitoxantrone, but any anthraquinone, anthrapyrazole, aza-anthraquinone and diaza-anthraquinone antitumor agent having two reactive amino groups in the molecule capable of forming amide linkages with the carbonyl groups of the dianhydride would be suitable for use in the present invention.

The conjugates of the invention have the distinct advantages of showing more long term survival, reduction of tumor size, and less toxicity at efficacious doses when compared to free anticancer agents in animal models of tumors.

The therapeutic compositions of the present invention induce palliation of leukemia and related cancers in mammals when administered in amounts ranging from about 5 mg to about 25 mg of drug equivalent per kilogram of body weight per day. A preferred dosage regimen for optimum results would be from about 5 mg to about 20 mg per kilogram of body weight per day, and such dosage units are employed that a total of from about 350 mg to about 1.4 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation.

The pharmaceutical compositions of the invention may be administered intravenously, parenterally, intraperitoneally or as surgical implants. Solutions as free acid or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients for those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit contains a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier dosage form can, for example, contain the principal active compounds in amounts ranging from about 0.1 to about 1750 mg, with from about 1 to about 1400 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

Palliation of cancers are attained, for example, using intravenous administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid palliation of the leukemia or the like, in the absence of excessive deleterious side effects of a cytoxic nature to the hosts harboring the cancer. As used herein, cancer disease means blood malignancies such as leukemia, as well as other solid malignancies such as breast tumors and others. Palliation is the arresting or retarding the growth of the tumor or other manifestation of the disease compared to the course of the disease in the absence of treatment.

The novel compositions of the present invention possess the property of inducing palliation of cancer diseases in mammals as established by the following tests wherein mitoxantrone was used as the antitumor agent in the composition.

Lymphocytic Leukemia P388 Test

In the P388 murine leukemia tests, male CDF1 mice weighing 18 to 21 g are injected intraperitoneally (ip) with $1 \times 10^6$ P388 tumor cells on day 0 of the test. Drugs are administered by iv, sc or ip routes at days 1, 5 and 9 post tumor inoculation. Five to ten mice per group are used. The effect on survival is expressed as %ILS which is calculated as follows: ILS=[(T/C)−1]×100, where T/C is the median survival time (MST) of mice in the treated group (T) divided by the MST of the placebo treated control group (C). A value of %ILS equivalent to 25% or greater indicates positive drug activity.

The polymeric derivative of mitoxantrone, MITO-BOETDA, is tested for its effect against the P388 tumor in a dose range of 1.5 to 20 mg/kg and shows dose dependent antitumor activity in the test (Table 1, FIGS. I, II, and III). MITO-BOETDA is poly[[(2-hydroxyethyl) -imino]carbonyl(3,6-dicarboxybicyclo[2.2.2]octa-7-ene -2,5-diyl)carbonyl[(2-hydroxyethyl)imino]-1,2-ethanediylimino (9,10-dihydro-5,8-dihydroxy-9,10-dioxo-1,4-anthracenediyl)imino-1,2-ethanediyl disodium salt].

The polymeric derivative of mitoxantrone, MITO-CBTCDA, is tested for its effect against the P388 tumor in a dose range of 2.9 to 29.1 mg/kg and shows dose dependent antitumor activity in the test (Table 6, FIG. XVI). MITO-CBTCDA is poly[[(2-hydroxyethyl)imino]carbonyl-2,4-dicarboxy-1,3-cyclobutanediyl)carbonyl [(2-hydroxyethyl)imino]-1,2-ethanediylimino (9,10-dihydro-5,8-dihydroxy-9,10-dioxo-1,4-anthracenediyl)imino-1,2-ethanediyl disodium salt].

The polymeric derivative of mitoxantrone, MITO-BTCDA, is tested for its effect against the P388 tumor in a dose range of 1.5 to 15 mg/kg and shows dose dependent antitumor activity in the test (Table 7, FIG. XVII). MITO-BTCDA is poly[[(2-hydroxyethyl)imino]-carbonyl-2,5-dicarboxy-1,4-phenylene)carbonyl[(2-hydroxyethyl)imino]-1, 2-ethanediylimino(9,10-dihydro -5,8-dihydroxy-9,10-dioxo-1,4-anthracenediyl)imino-1,2-ethanediyl disodium salt].

TABLE 1

TEST FOR CYTOTOXIC ANTITUMOR ACTIVITY AGAINST P388 LEUKEMIA
(DRUG SENSITIVE TUMOR)

| COMPOUND | DOSE MG/KG/DOSE | TREAT. SCHED. | MEDIAN SURVIVAL TIME (RANGE) | % ILS | 60 DAYS S/T |
|---|---|---|---|---|---|
| Placebo | — | 1, 5, 9 | 11.0 (10–11) | — | 0/10 |
| Mitoxantrone | 6.0 | 1, 5, 9 IV | 13.0 (12–16) | +18 | 0/5 |
| (free) | 3.0 | 1, 5, 9 IV | 27.0 (16–49) | +145 | 0/5 |
|  | 1.5 | 1, 5, 9 IV | 25.0 (24–30) | +127 | 0/5 |
| Mito-BOETDA | 20.0 | 1, 5, 9 IV | 60.0 (34–60) | +445 | 4/5 |
| (polymer) | 15.0 | 1, 5, 9 IV | 60.0 (28–60) | +445 | 4/5 |
|  | 10.0 | 1, 5, 9 IV | 60.0 (48–60) | +445 | 4/5 |
|  | 6.0 | 1, 5, 9 IV | 25.0 (20–60) | +127 | 1/5 |
|  | 3.0 | 1, 5, 9 IV | 19.0 (17–20) | +73 | 0/5 |
| Mitoxantrone | 6.0 | 1, 5, 9 SC | 37.0 (15–60) | +236 | 2/5 |
| (free) | 3.0 | 1, 5, 9 SC | 28.0 (24–37) | +154 | 0/5 |
|  | 1.5 | 1, 5, 9 SC | 20.0 (16–23) | +82 | 0/5 |
| Mito-BOETDA | 20.0 | 1, 5, 9 SC | 60.0 (24–60) | +445 | 4/5 |
| (polymer) | 15.0 | 1, 5, 9 SC | 35.0 (29–60) | +218 | 2/5 |
|  | 10.0 | 1, 5, 9 SC | 31.0 (25–60) | +182 | 1/5 |
|  | 6.0 | 1, 5, 9 SC | 23.0 (22–38) | +109 | 0/5 |
|  | 3.0 | 1, 5, 9 SC | 18.0 (16–19) | +64 | 0/5 |
| Mitoxantrone | 6.0 | 1, 5, 9 IP | 13.0 (12–14) | +18 | 0/5 |
| (free) | 3.0 | 1, 5, 9 IP | 19.0 (19–24) | +73 | 0/5 |
|  | 1.5 | 1, 5, 9 IP | 26.0 (20–60) | +136 | 1/5 |
| Mito-BOETDA | 20.0 | 1, 5, 9 IP | 60.0 (0) | +445 | 5/5 |
| (polymer) | 15.0 | 1, 5, 9 IP | 60.0 (0) | +445 | 5/5 |
|  | 10.0 | 1, 5, 9 IP | 60.0 (26–60) | +445 | 3/5 |
|  | 6.0 | 1, 5, 9 IP | 26.0 (22–60) | +136 | 0/5 |
|  | 3.0 | 1, 5, 9 IP | 20.0 (19–34) | +82 | 0/5 |

MX-1: This breast carcinoma is a duct cell carcinoma xenograft transplant from the Division of Cancer Treatment and the Division of Cancer Prevention of the National Cancer Institute. It is carried as fragments in donor mice. For implantation into test nude mice, the tumors are removed and cut into 1 mm fragments, five of which are implanted subcutaneously in each test mouse. Tumors are staged and animals are sorted when the tumors reach a size of 100–150 mg. Treatments are administered at days 1, 5 and 9 post tumor staging. The effect on the tumor growth is expressed as %T/C which is the relative tumor growth of treated group (T) divided by the relative tumor growth of saline control (C). A value of %T/C equivalent to 42% or less is considered active.

The polymeric derivative of mitoxantrone, MITO-BOETDA, is tested side by side with free mitoxantrone for comparing their effect against MX-1 breast tumor. MITO-BOETDA is poly[[(2-hydroxyethyl)imino]-carbonyl (3,6-dicarboxybicyclo[2.2.2]octa-7-ene-2,5-diyl)carbonyl [(2- hydroxyethyl)imino]-1,2-ethanediylimino (9,10-dihydro-5, 8-dihydroxy-9,10-dioxo-1,4-anthracenediyl)imino-1,2-ethanediyl disodium salt]. The data are shown in Table 2, FIGS. IV, V and VI.

TABLE 2

Antitumor activity of MITO-BOETDA polymer vs MX-1

| Drug | Dosage[a] (mg/kg) | Relative Tumor mass[b] % T/C | Survival |
|---|---|---|---|
| MITO-BOETDA polymer | 20 | 41 | 5/5 |
|  | 15 | 42 | 5/5 |
|  | 10 | 49 | 5/5 |
|  | 6 | 59 | 5/5 |
|  | 3 | 82 | 5/5 |
| MITO | 3.0 | 39 | 4/5 |
|  | 1.5 | 72 | 5/5 |

[a]Three doses were given to nude mice by iv administration on days 8, 12 and 16 post tumor implantation.
[b]At day 35 post tumor implantation.

| Drug | Dosage[a] (mg/kg) | Relative Tumor mass[b] % T/C | Survival |
|---|---|---|---|
| MITO-BOETDA polymer | 20 | 25 | 5/5 |
|  | 15 | 44 | 5/5 |
|  | 10 | 43 | 5/5 |
|  | 6 | 57 | 5/5 |
|  | 3 | 71 | 5/5 |
| MITO | 3 | 62 | 5/5 |
|  | 1.5 | 64 | 5/5 |

[a]Three doses were given to nude mice by sc administration on days 8, 12 and 16 post tumor implantation.
[b]At day 35 post tumor implantation.

| Drug | Dosage[a] (mg/kg) | Relative Tumor mass[b] % T/C | Survival |
|---|---|---|---|
| MITO-BOETDA polymer | 20 | 34 | 5/5 |
|  | 15 | 35 | 5/5 |
| MITO | 3 | — | 0/5 |
|  | 1.5 | 61 | 5/5 |

[a]Three doses were given to nude mice by ip administration on days 8, 12 and 16 post tumor implantation.
[b]At day 35 post tumor implantation.

MCF-7: This is a breast adenocarcinoma pleural effusion from the ATCC(American Type Culture Collection, ATCC line # HTB 22). It is carried as fragments in donor mice. For implantation into test nude mice, the tumors are removed and cut into i mm fragments, five of which are implanted subcutaneously in each test mouse. Tumors are staged and animals are sorted when the tumors reach a size of 100–150 mg. Treatments are administered at days 1, 5 and 9 post tumor staging. The effect on the tumor growth is expressed as %T/C which is the relative tumor growth of treated group (T) divided by the relative tumor growth of saline control (C). A value of %T/C equivalent to 42% or less is considered active.

The polymeric derivative of mitoxantrone, MITO-BOETDA, is tested side by side with free mitoxantrone for comparing their effect against MCF-7 breast tumor. MITO-BOETDA is poly[[(2-hydroxyethyl)imino]carbonyl (3,6-dicarboxybicyclo[2.2.2]octa-7-ene-2,5-diyl)carbonyl [(2-hydroxyethyl)imino]-1,2-ethanediyl -imino(9,10-dihydro-5,8-dihydroxy-9,10-dioxo-1,4-anthracenediyl) imino-1,2-ethanediyl disodium salt]. The data are shown in Table 3, FIGS. VII, VIII and IX.

TABLE 3

Antitumor activity of MITO-BOETDA polymer vs MCF7

| Drug | Dosage[a] (mg/kg) | Relative Tumor mass[b] % T/C | Survival |
|---|---|---|---|
| MITO-BOETDA polymer | 15 | 43 | 5/5 |
|  | 10 | 53 | 5/5 |
|  | 6 | 74 | 5/5 |
| MITO | 3.0 | 68 | 4/5 |
|  | 2.4 | 85 | 5/5 |

[a]Three doses were given to nude mice by iv administration on days 10, 14 and 18 post tumor implantation.
[b]At day 45 post tumor implantation.

| Drug | Dosage[a] (mg/kg) | Relative Tumor mass[b] % T/C | Survival |
|---|---|---|---|
| MITO-BOETDA polymer | 20 | 41 | 5/5 |
|  | 15 | 66 | 5/5 |
|  | 10 | 82 | 5/5 |
|  | 6 | 83 | 5/5 |
| MITO | 2 | 84 | 5/5 |
|  | 1.5 | 99 | 5/5 |

[a]Three doses were given to nude mice by ip administration on days 10, 14 and 18 post tumor implantation.
[b]At day 45 post tumor implantation.

| Drug | Dosage[a] (mg/kg) | Relative Tumor mass[b] % T/C | Survival |
|---|---|---|---|
| MITO-BOETDA polymer | 20 | 53 | 2/5 |
|  | 15 | 55 | 5/5 |
|  | 10 | 58 | 5/5 |
|  | 6 | 65 | 5/5 |
| MITO | 2.4 | 98 | 5/5 |
|  | 1.5 | 94 | 5/5 |

[a]Three doses were given to nude mice by sc administration on days 10, 14 and 18 post tumor implantation.
[b]At day 45 post tumor implantation.

OVCAR3: There is a human ovary adenocarcinoma and obtained from ATCC line #HTB 161 and is used as an ascites tumor. The ascites are harvested from donor mice, and $8 \times 10^6$ cells are implanted subcutaneously into nude mice. As above, the tumor is staged to a size of 100–150 mg prior to drug treatment. Mice are treated with the tested drugs by intraperitoneal, intravenous or subcutaneous administration at several dose level, every 4 days for a total of three doses, starting one day after tumor staging. Each test group has five mice, a control group of ten mice. Tumor mass is determined by measuring the tumor diameter once weekly for at least four cycles post tumor staging. The effect on the tumor growth is expressed as %T/C which is the relative tumor growth of treated group (T) divided by the relative tumor growth of saline control (C). A value of %T/C equivalent to 42% or less is considered active.

The polymeric derivative of mitoxantrone, MITO-BOETDA, is tested side by side with free mitoxantrone for comparing their effect against OVCAR3 ovarian tumor. MITO-BOETDA is poly[[(2-hydroxyethyl)imino]carbonyl (3,6-dicarboxybicyclo[2.2.2]octa-7-ene-2,5-diyl) carbonyl [(2-hydroxyethyl)imino]-1,2-ethanediylimino (9,10-dihydro-5,8-dihydroxy-9,10-dioxo-1,4-anthracenediyl)imino-1,2-ethanediyl disodium salt]. The data are shown in Table 4, FIGS. X, XI and XII.

TABLE 4

Antitumor activity of MITO-BOETDA polymer vs OVCAR3

| Drug | Dosage[a] (mg/kg) | Relative Tumor mass[b] % T/C | Survival |
|---|---|---|---|
| MITO-BOETDA polymer | 20 | 71 | 1/5 |
|  | 15 | 61 | 5/5 |
|  | 10 | 72 | 5/5 |
|  | 6 | 90 | 5/5 |
|  | 3 | 110 | 5/5 |
| MITO | 3.0 | 68 | 4/5 |

[a]Three doses were given to nude mice by iv administration on days 6, 10 and 14 post tumor implantation.
[b]At day 33 post tumor implantation.

| Drug | Dosage[a] (mg/kg) | Relative Tumor mass[b] % T/C | Survival |
|---|---|---|---|
| MITO-BOETDA polymer | 20 | — | 0/5 |
|  | 15 | 56 | 5/5 |
|  | 10 | 67 | 5/5 |
|  | 6 | 97 | 5/5 |
|  | 3 | 107 | 5/5 |
| MITO | 3 | 63 | 5/5 |
|  | 1.5 | 100 | 5/5 |

[a]Three doses were given to nude mice by sc administration on days 6, 10 and 14 post tumor implantation.
[b]At day 33 post tumor implantation.

| Drug | Dosage[a] (mg/kg) | Relative Tumor mass[b] % T/C | Survival |
|---|---|---|---|
| MITO-BOETDA polymer | 20 | — | 0/5 |
|  | 15 | 59 | 5/5 |
|  | 10 | 105 | 5/5 |
|  | 6 | 97 | 5/5 |
|  | 3 | 100 | 5/5 |
| MITO | 3 | 74 | 4/5 |

[a]Three doses were given to nude mice by ip administration on days 6, 10 and 14 post tumor implantation.
[b]At day 33 post tumor implantation.

CO77: This colon tumor is a carcinoma xenograft transplant from American Cyanamid Company (ACCO). This is carried as fragments in donor mice. For implantation into test nude mice, the tumors are removed and cut into 1 mm fragments, five of which are implanted subcutaneously in each test mouse. Tumors are staged and animals are sorted when the tumors reach a size of 100–150 mg. Treatments are administered at day 1, 5 and 9 post tumor staging. The effect on the tumor growth is expressed as %T/C which is the relative tumor growth of treated group (T) divided by the relative tumor growth of saline control (C). A value of %T/C equivalent to 42% or less is considered active.

The polymeric derivative of mitoxantrone, MITO-BOETDA, is tested side by side with free mitoxantrone for comparing their effect against CO77 colon tumor. MITO-BOETDA is poly[[(2-hydroxyethyl)imino]carbonyl (3,6-dicarboxybicyclo[2.2.2]octa-7-ene-2,5-diyl) carbonyl[(2-hydroxyethyl)imino]-1,2-ethanediylimino (9,10-dihydro-5,8-dihydroxy-9,10-dioxo-1,4-anthracenediyl)imino-1,2-ethanediyl disodium salt]. The data are shown in Table 5, FIGS. XIII, XIV and XV.

TABLE 5

Antitumor activity of MITO-BOETDA polymer vs CO77

| Drug | Dosage[a] (mg/kg) | Relative Tumor mass[b] % T/C | Survival |
|---|---|---|---|
| MITO-BOETDA polymer | 15 | 24 | 2/5 |
|  | 10 | 49 | 4/5 |
|  | 6 | 52 | 5/5 |
| MITO | 3.0 | 52 | 4/5 |
|  | 2.4 | 52 | 5/5 |

[a]Three doses were given to nude mice by iv administration on days 10, 14 and 18 post tumor implantation.
[b]At day 30 post tumor implantation.

| Drug | Dosage[a] (mg/kg) | Relative Tumor mass[b] % T/C | Survival |
|---|---|---|---|
| MITO-BOETDA polymer | 15 | 36 | 5/5 |
|  | 10 | 58 | 5/5 |
|  | 6 | 68 | 5/5 |
| MITO | 1.6 | 58 | 5/5 |
|  | 1.0 | 75 | 5/5 |

[a]Three doses were given to nude mice by ip administration on days 10, 14 and 18 post tumor implantation.
[b]At day 30 post tumor implantation.

| Drug | Dosage[a] (mg/kg) | Relative Tumor mass[b] % T/C | Survival |
|---|---|---|---|
| MITO-BOETDA polymer | 15 | 48 | 4/5 |
|  | 10 | 69 | 5/5 |
| MITO | 3 | 76 | 5/5 |

[a]Three doses were given to nude mice by sc administration on days 10, 14 and 18 post tumor implantation.
[b]At day 30 post tumor implantation.

TABLE 6

TEST FOR CYTOTOXIC ANTITUMOR ACTIVITY AGAINST P388 LEUKEMIA

| COMPOUND | DOSE MG/KG/DOSE | TREAT. SCHED. | MEDIAN SURVIVAL TIME (RANGE) | % ILS |
|---|---|---|---|---|
| Placebo | 0 | 1, 5, 9 | 10.0 (9–11) | — |
| Mitoxantrone | 4.1 | 1, 5, 9 IP | 17.0 (14–25) | +70 |
|  | 2.1 | 1, 5, 9 IP | 25.0 (18–29) | +150 |
| Mitoxantrone-CBTCDA (Polymer) | 29.1 | 1, 5, 9 IP | 20.0 (19–25) | +100 |
|  | 23.3 | 1, 5, 9 IP | 26.0 (19–30) | +160 |
|  | 17.5 | 1, 5, 9 IP | 19.0 (17–21) | +90 |
|  | 11.6 | 1, 5, 9 IP | 19.0 (17–22) | +90 |
|  | 5.8 | 1, 5, 9 IP | 19.0 (16–28) | +90 |
|  | 2.9 | 1, 5, 9 IP | 16.0 (15–21) | +60 |

TABLE 7

TEST FOR CYTOTOXIC ANTITUMOR ACTIVITY AGAINST P388 LEUKEMIA

| COMPOUND | DOSE MG/KG/DOSE | TREAT. SCHED. | MEDIAN SURVIVAL TIME (RANGE) | % ILS |
|---|---|---|---|---|
| Placebo | — | 1, 5, 9 | 10.0 (9–11) | — |
| Mitoxantrone | 9.0 | 1, 5, 9 IP | 13.0 (12–14) | +30 |
|  | 6.0 | 1, 5, 9 IP | 13.0 (12–13) | +30 |
|  | 3.0 | 1, 5, 9 IP | 24.0 (20–28) | +140 |
|  | 1.5 | 1, 5, 9 IP | 29.0 (19–30) | +190 |
| Mitoxantrone- | 15.0 | 1, 5, 9 IP | 21.0 (19–30) | +110 |
| BTCDA | 12.0 | 1, 5, 9 IP | 19.0 (18–30) | +90 |
| (Polymer) | 9.0 | 1, 5, 9 IP | 19.0 (18–20) | +90 |
|  | 6.0 | 1, 5, 9 IP | 19.0 (18–25) | +90 |
|  | 3.0 | 1, 5, 9 IP | 15.0 (14–19) | +50 |
|  | 1.5 | 1, 5, 9 IP | 15.0 (15–19) | +50 |

The compounds of this invention and their preparation are illustrated by the following non-limiting examples.

EXAMPLE 1

Poly[[(2
-hydroxyethyl)imino]carbonyl(3,6-dicarboxybicyclo
[2.2.2]octa-7-ene-2,5-diyl)carbonyl[(2-hydroxyethyl)
imino]-1,2-ethanediylimino(9,10-dihydro-5,8-
dihydroxy-9,10-dioxo-1,4-anthracenediyl)imino-1,2-
ethanediyl disodium salt]

A solution of 100 mg of 5,8-dihydroxy-1,4bis [[2-[(2-hydroxyethyl)amino]ethyl]amino]-9,10-anthracenedione in 1 ml of 1-methyl-2-pyrrolidinone is stirred while a solution of 55.85 mg of bicyclo[2.2.2]octa-7-ene-2,3,5,6-tetracarboxylic dian-hydride in 1 ml of 1-methyl-2-pyrrolidinone is added dropwise. An additional 1 ml of 1-methyl-2-pyrrolidinone is added to rinse all of the dianhydride into the reaction solution. After stirring for 18 hours at room temperature, the reaction solution is monitored by TLC on a silica gel plate developed in a mixed solvent (DMF:methylcellosolve:THF:i-PrOH:CH$_3$CN; NH$_4$OH:HOAc-4:3:3:2:2:1:1). It shows that the polymer solution stays at the origin of the plate, whereas mitoxantrone moves on the TLC plate with an Rf value of 0.6. The solvent is removed in vacuo to yield a deep blue residue which is stirred with ether, the solid is collected and washed with 100 ml of ether. The solid is dried in vacuo for 18 hours to afford 169.7 mg of the desired product as a deep blue solid:

IR (KBr) 3399, 3058, 2874, 1729, 1642, 1608, 1563, 1516, 1455, 1395, 1352, and 1197 cm$^{-1}$; MALDI/MS (max-tix-assisted laser desorption/ionization mass spectrometry) peak MW 10.8 KD; $^1$H NMR (DMF-d$_7$) d 3.25 (4H, b, allylic protons, CH-CON-), 3.4 (2H, b, CH-COOH), 3.5 (4H, b, -N-CH$_2$-CH$_2$OH), 3.6 (4H, b, CH-N-CH$_2$CH$_2$OH), 3.74 (4H, b, Ar-NH-CH$_2$), 3.83 (4H, b, CH$_2$-OH), 4.05 (2H, b, CH$_2$-OH), 6.3 (2H, m, vinyl protons), 7.15 (2H, s, m, 6,7-H), 7.75 (2H, m, 2,3-H), 10.6 (2H, b, Ar-NH), and 13.55 (2H, b, Ar-OH).

A 120 mg portion of this blue solid is neutralized to pH 7.2 with 1% aqueous sodium bicarbonate. After filtration, the solution is lyophilized to give 122 mg of blue powder, containing 55 mg of mitoxantrone.

EXAMPLE 2

Poly[[(2-hydroxyethyl)imino]carbonyl-1,4-dicarboxy-
1,3cyclobutanediyl)carbonyl[(2-hydroxyethyl)imino]-
1,2-ethanediylimino
(9,10-dihydro-5,8-dihydroxy-9,10-dioxo
-1,4-anthracenediyl)imino-1,2-ethanediyl
disodium salt]

A solution of 100 mg of 5,8-dihydroxy-1,4bis [[2-[(2-hydroxyethyl)amino]ethyl]amino]-9,10-anthracenedione in 1 ml of 1-methyl-2-pyrrolidinone is stirred while a solution of 45.5 mg of 1,2,3,4-cyclobutane-tetracarboxylic dianhydride in 1 ml of 1-methyl-2-pyrrolidinone is added drowise. An additional 0.5 ml of 1-methyl-2-pyrrolidinone is added to rinse all the dianhydride into the reaction solution. After stirring for 18 hours at room temperature, the reaction solution is monitored by TLC on a silica gel plate developed in a mixed solvent (DMF:methylcellosolve:THF:i-PrOH:CH$_3$CN: NH$_4$OH:HOAc-4:3:3:2:2:1:1:). The solvent is removed in vacuo to a deep blue residue which is stirred with ether, the solid is collected and washed with 100 ml of ether. The solid is dried in vacuo for 18 hours to afford 181.9 mg of the desired product as a deep blue solid:

IR (KBr) 3422, 2921, 2853, 1729, 1638, 1607, 1562, 1515, 1453, 1400, 1351, and 1203 cm$^{-1}$; MALDI/MS peak MW 12.2 KD; $^1$H NMR (DMF-d$_7$) d 3.5 (10H, b, CH$_2$-N-CH$_2$-CH$_2$OH, CH-CON-), 3.65 (2H, b, CH-COOH), 3.75 (8H, b, CH$_2$-CH$_2$-N-CH$_2$-CH$_2$-OH), 4.2 (2H, b, CH$_2$OH), 7.1 (2H, m, 6,7-H), 8.05 (2H, m, 2,3-H), 10.6 (2H, b, Ar-NH), and 13.5 (2H, b, Ar-OH).

A 97 mg portion of this blue solid is neutralized to pH 7.2 with 1% aqueous sodium bicarbonate. After filtration, the solution is lyophilized to give 95 mg of blue powder, containing 25.8 mg of mitoxantrone.

EXAMPLE 3

Poly[[(2-hydroxyethyl)imino]carbonyl(2,5-dicarboxy-
1,4-phenylene)carbonyl[(2-hydroxyethyl)imino]-1,2-
ethanediylimino
(9,10-dihydro-5,8-dihydroxy-9,10-dioxo
-1,4-anthracenediyl)imino-1,2-ethanediyl
disodium salt]

A solution of 100 mg of 5,8-dihydroxy-1,4-bis[[2-[(2-hydroxyethyl)amino]ethyl]amino]-9,10-anthracenedione in 1 ml of 1-methyl-2-pyrrolidinone is stirred while a solution of 50.6 mg of 1,2,4,5-benzenetetracarboxylic dianhydride in 1 ml of 1-methyl-2-pyrrolidinone is added dropwise. An additional 1.0 ml of 1-methyl-2-pyrrolidinone is added to rinse all the dianhydride into the reaction solution. After stirring for 18 hours at room temperature, the reaction solution is monitored by TLC on a silica gel plate developed in a mixed solvent (DMF: methylcellosolve:THF:i-PrOH:CH$_3$CN:-NH$_4$OH:HOAc-4:3:3:2:2:1:1). The solvent is removed in vacuo to a yield deep blue residue which is stirred with ether, the solid is collected and washed with 100 ml of ether. The solid is dried in vacuo for 18 hours to afford 187 mg of the desired product as a deep blue solid:

IR (KBr) 3412, 3026, 2926, 1719, 1635, 1607, 1562, 1514, 1457, 1402, 1351, 1301, 1259, and 1203; MALDI/MS peak MW 12.2 KD; $^1$H NMR (DMF-d$_7$) d 3.5 (4H, b, -N-CH$_2$-CH$_2$OH), 3.6 (4H, b, CH$_2$-N-CH$_2$CH$_2$OH), 3.87 (8H, b, CH$_2$-CH$_2$-N-CH$_2$-CH$_2$-OH), 4.16 (2H, b, CH$_2$OH), 7.15 (2H, m, 6,7-H), 7.9 (2H, m, 2,3-H), 8.0 (2H, s, Ar-3',6'-H), 10.5 (2H, b, Ar-NH), and 13.5 (2H, b, Ar-OH).

A 120 mg portion of this blue solid is neutralized to pH 7.4 with 1% aqueous sodium bicarbonate. After filtration, the solution is lyophilized to give 119 mg of blue powder, containing 56.9 mg of mitoxantrone.

A Description of the Polymers

The molecular weights of all polymers of the invention are determined by MALDI/MS (matrix-assisted laser desorption/ionization mass spectrometry) as indicated in Examples 1–3. The polymerization procedure given in the Examples does not yield a polymer with a uniform molecular weight, rather it generates a polymer with a bell-shaped distribution of molecular weights ranging from ~1,000 to ~160,000. The peak molecular weights of the polymers are measured from the mass spectra and shown in Examples 1–3. In Example 1, the most abundant molecular weight of the MITO-BOETDA polymer is ~10,800 (z~15), though the mass spectrum analysis indicates species with z~1 to z~217 in the product. Likewise, the other MITO-dianhydride polymer MITO-CBTCDA in Example 2 is a mixture of species with z~1 to z~234, wherein the most abundant molecular weight is ~12,200 (z~18). The most abundant molecular weight of the other MITO-dianhydride polymer MITO-BTCDA in Example 3 is ~12,200 (z~19), though the mass spectrum analysis shows species with z~1 to z~242.

The end groups of the polymers are H on the left and OH on the right of the formula, since mitoxantrone is reacted with one equivalent amount of dianhydride. For example, the simplest situation is where z=1 in the generic formula. One molecule of mitoxantrone reacts with one molecule of dianhydride to give a molecule of product which upon hydrolysis and neutralization would afford MITO-BOETDA, where the end groups are H and OH, as shown in the following scheme. The one amine group and one carboxylic acid group on either end of the polymer would exist as a zwitterion form in neutral aqueous solution.

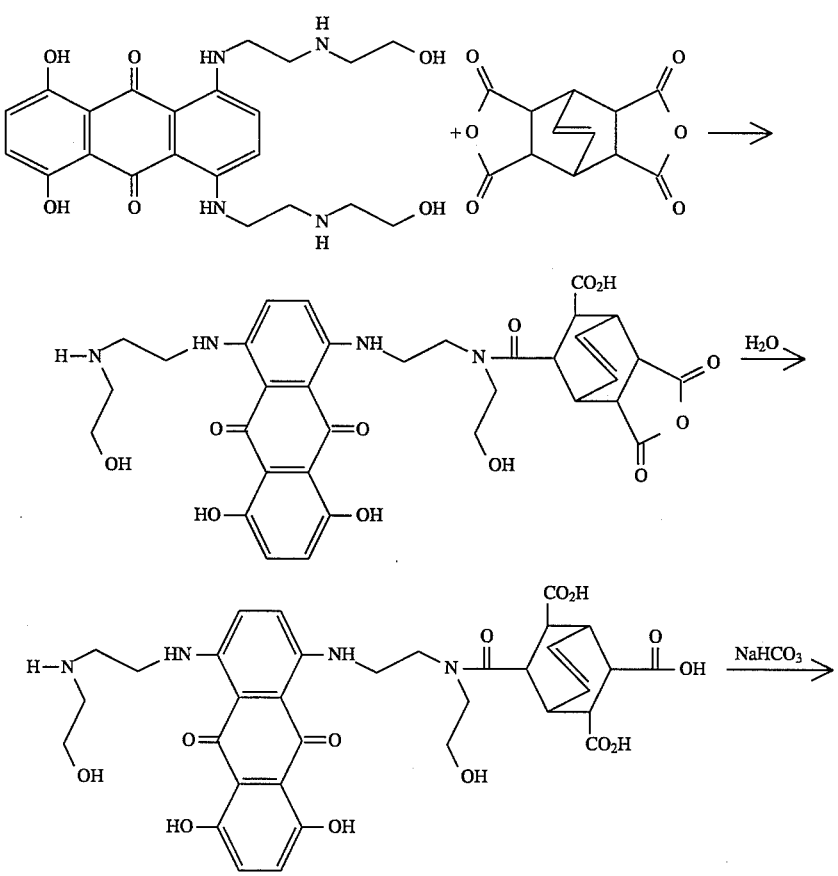

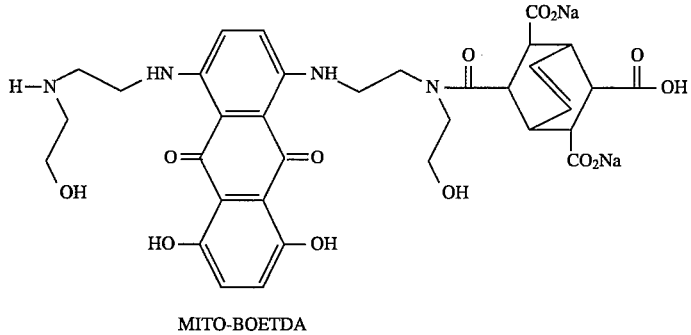

MITO-BOETDA

I claim:

1. A mixture of polymers which comprises a H end group on the left and an OH end group on the right and a chain, the ends of which are bonded to the respective end units, of the formula:

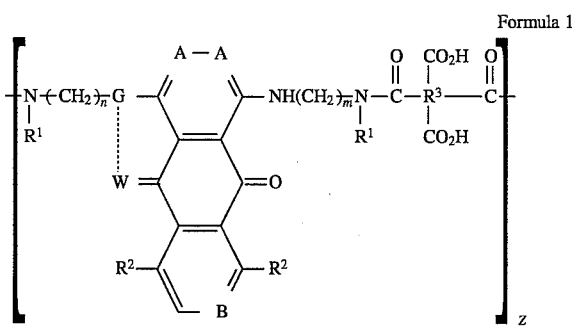

Formula 1 wherein
A and B are CH or N, and when B is N, A is CH;
the dotted line is an optional bond;
W is O or N, and when W is O, G is NH, and when W is N, G is N and the dotted line is a bond;
$R^1$ is the same or different and is selected from H, -(CH$_2$)$_n$OH, straight or branched lower alkyl (C$_1$-C$_4$), and carbocyclic rings of 3, 4, 5, 6, or 7 carbon atoms;
$R^2$ is the same or different and selected from hydrogen, OR, halogen, or -NRR';
R and R' are the same or different and selected from H or lower alkyl (C$_1$-C$_4$);
m and n are the same or different and are 2 or 3;
Z is 1–250; and
the moiety

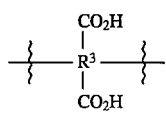

is a bicyclic ring having the structure:

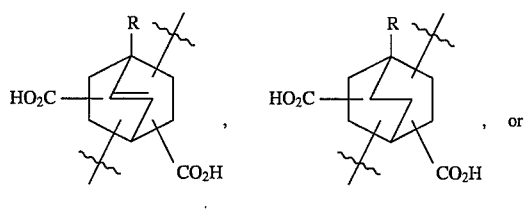

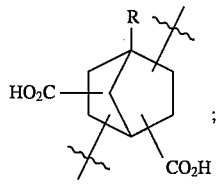

wherein R is H or lower alkyl (C$_1$-C$_4$);
or a pharmaceutically acceptable salt thereof.

2. The compound according to claim 1 wherein said salts are selected from potassium, sodium, calcium, magnesium or ammonium.

3. The polymer of claim 2, wherein the moiety

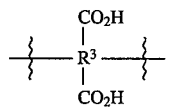

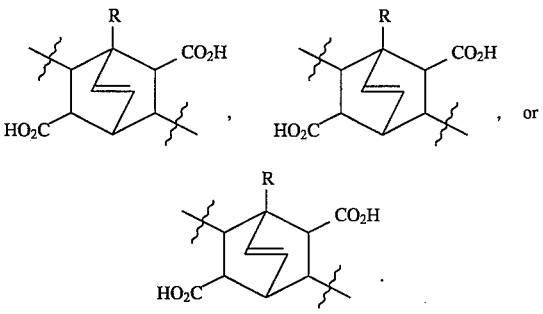

4. The compound according to claim 3 wherein the moiety

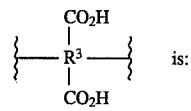

is:

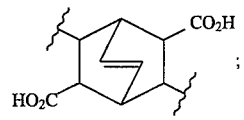

n is 2; and Z is 5–25.

5. The compound according to claim 4 wherein A and B are CH; W is O and G is NH.

6. The compound according to claim 4 wherein A and B are CH; W is N; G is N and the dotted line is a bond.

7. The compound according to claim 4 wherein A is CH; B is N; W is O; G is NH.

8. The compound according to claim 4 wherein A is N; B is CH; W is O; G is NH.

9. A pharmaceutical composition useful for treating leukemia and solid tumors in a mammal comprising a suitable pharmaceutical carrier and an effective amount of a compound of claim 1.

10. A method of treating solid tumors in a mammal which comprises administering to said mammal a therapeutically effective amount of a compound of claim 1.

11. A method of inducing regression of leukemia and/or inhibiting tumor growth in a mammal which comprises administering to said mammal a therapeutically effective amount of a compound of claim 1.

12. The compound according to claim 5 Poly[[2-hydroxyethyl)imino]carbonyl(3,6-dicarboxybicyclo [2.2.2]-oct-7-ene-2,5-diyl)carbonyl[(2-hydroxyethyl) imino]-1,2-ethanediylimino(9,10-dihydro-5,8-dihydroxy-9,10-dioxo-1,4-anthracenediyl)imino-1,2-ethanediyl disodium salt, wherein Z is approximately 1 to 217].

13. The compound according to claim 5 Poly[[2-hydroxyethyl)imino]carbonyl(3,6-dicarboxybicyclo [2.2.2]-oct-7-ene-2,5-diyl)carbonyl[(2-hydroxyethyl) imino]-1,2-ethanediylimino(9,10-dihydro-5,8-dihydroxy-9,10-dioxo-1,4-anthracenediyl) imino-1,2-ethanediyl, wherein Z is approximately 1 to 217.

* * * * *